(12) United States Patent
Shelton et al.

(10) Patent No.: US 10,952,601 B2
(45) Date of Patent: *Mar. 23, 2021

(54) OTOSCOPE TIP AND METHODS OF USE

(71) Applicant: PhotoniCare, Inc., Champaign, IL (US)

(72) Inventors: Ryan Shelton, Champaign, IL (US); Ryan Nolan, Urbana, IL (US)

(73) Assignee: PhotoniCare, Inc., Champaign, IL (US)

( * ) Notice: Subject to any disclaimer, the term of this patent is extended or adjusted under 35 U.S.C. 154(b) by 93 days.

This patent is subject to a terminal disclaimer.

(21) Appl. No.: 16/243,685

(22) Filed: Jan. 9, 2019

(65) Prior Publication Data

US 2019/0142258 A1    May 16, 2019

Related U.S. Application Data

(63) Continuation-in-part of application No. 15/806,653, filed on Nov. 8, 2017, now Pat. No. 10,278,570, which is a continuation of application No. PCT/US2016/031450, filed on May 9, 2016.

(60) Provisional application No. 62/158,765, filed on May 8, 2015.

(51) Int. Cl.
```
A61B 1/227    (2006.01)
A61B 1/32     (2006.01)
A61B 1/00     (2006.01)
```

(52) U.S. Cl.
CPC ........ *A61B 1/2275* (2013.01); *A61B 1/00091* (2013.01); *A61B 1/00101* (2013.01); *A61B 1/00105* (2013.01); *A61B 1/00142* (2013.01); *A61B 1/32* (2013.01); *A61B 1/00128* (2013.01)

(58) Field of Classification Search
CPC .......... A61B 1/227; A61B 1/2275; A61B 1/32
See application file for complete search history.

(56) References Cited

U.S. PATENT DOCUMENTS

| | | | |
|---|---|---|---|
| 3,110,304 A | 11/1963 | Hartman | 128/9 |
| 4,380,998 A | 4/1983 | Kieffer, III et al. | 128/9 |
| 5,491,524 A | 2/1996 | Hellmuth et al. | 351/212 |
| 5,836,877 A | 11/1998 | Zavislan | 600/407 |
| 5,919,130 A * | 7/1999 | Monroe | A61B 1/227 600/129 |
| 5,921,926 A | 7/1999 | Rolland et al. | 600/407 |
| 5,994,690 A | 11/1999 | Kulkarni et al. | 250/216 |
| 7,289,842 B2 | 10/2007 | Maschke | 600/478 |
| 7,354,399 B2 | 4/2008 | Strom et al. | 600/200 |
| 7,406,346 B2 | 7/2008 | Kleen et al. | 600/424 |

(Continued)

FOREIGN PATENT DOCUMENTS

KR    1013443040000    12/2013    ......... A61C 1/08

OTHER PUBLICATIONS

International Preliminary Report on Patentability, PCT Application No. PCT/US2016/031450, pp. 1-6 (dated Nov. 23, 2017).

(Continued)

*Primary Examiner* — Julianna N Harvey
(74) *Attorney, Agent, or Firm* — J. Peter Paredes; Amin Talati Wasserman LLP

(57) ABSTRACT

Provided herein are systems, methods, and designs of speculum tips for pneumatic otoscopy. A speculum tip is disclosed and generally comprises: a cylindrical configuration including a narrow distal tip region longitudinally extending from a larger proximal region.

17 Claims, 20 Drawing Sheets

(56) References Cited

U.S. PATENT DOCUMENTS

| | | | |
|---|---|---|---|
| 7,949,385 B2 | 5/2011 | Khamene et al. | 600/416 |
| 8,115,934 B2 | 2/2012 | Boppart et al. | 356/479 |
| 8,135,453 B2 | 3/2012 | Slabaugh et al. | 600/473 |
| 8,197,403 B2 | 6/2012 | Strom et al. | 600/184 |
| 8,594,757 B2 | 11/2013 | Boppart et al. | 600/310 |
| 10,278,570 B2 * | 5/2019 | Shelton | A61B 1/32 |
| 2013/0060131 A1 | 3/2013 | Oghalai et al. | 600/425 |
| 2013/0214054 A1 * | 8/2013 | Faulkner | B05B 5/03 239/3 |
| 2013/0289353 A1 | 10/2013 | Seth et al. | A61B 1/277 |
| 2013/0300919 A1 | 11/2013 | Fletcher et al. | H04N 5/2254 |
| 2014/0012141 A1 | 1/2014 | Kim et al. | A61B 1/227 |

OTHER PUBLICATIONS

American Academy of Otolaryngology—Head and Neck Surgery. Fact Sheet: Ear Infection and Vaccines, 2014. https://www.entnet.org/HealthInformation/earInfectionVaccines.cfm.

Klein, J. O., Otitis Media. Clinical Infectious Diseases, vol. 19, No. 5: pp. 823-833, Nov. 1994.

Bartelds, A.I.M. et al., Acute Otitis Media In Adults: A Report From The International Primary Care Network. J Am Board Fam Pract, vol. 6, No. 4: pp. 333-339, Jul.-Aug. 1993.

Roberts J.E. et al., Ear Infections and Language Development. U.S. Dept. of Education, DOE Publication No. ECI-2000-9008, 2000.

Monasta, L. et al., Burden of Disease Caused by Otitis Media: Systematic Review and Global Estimates. PLoS One, vol. 7, Issue 4, e36226, Apr. 2012.

Hsu, G.S., et al., Management of otitis media using Agency for Health Care Policy and Research guidelines. The Agency for Health Care Policy and Research. Otolaryngology—Head Neck Surg, vol. 118, No. 4: pp. 437-443, Apr. 1998.

Lieberthal, A.S., et al., The Diagnosis and Management of Acute Otitis Media. Pediatrics, vol. 131, No. 3: e964-99, Mar. 2013.

Jones W.S., et al., How Helpful Is Pneumatic Otoscopy in Improving Diagnostic Accuracy? Pediatrics, vol. 112, No. 3; pp. 510-513. Sep. 2003.

Morris E, et al., Development and Validation of a Novel Ear Simulator to Teach Pneumatic Otoscopy. Simulation in Healthcare. vol. 7, No. 1, pp. 22-26. Feb. 2012.

Shekelle, G.T., et al, Diagnosis, Natural History, and Late Effects of Otitis Media with Effusion. Evidence Reports/Technology Assessments, No. 55, Sections 1 and 4, 2002.

Burrows, H.L., Otitis Media, Guidelines for Clinical Care Ambulatory, UMHS Otitis Media Guideline. Apr. 2013.

Hawkins, M., A Survey of America's Physicians: Practice Patterns and Perspectives. The Physicians Foundation, Sep. 2012.

Subcommittee on Management of Acute Otitis Media. Diagnosis and Management of Acute Otitis Media, Pediatrics, vol. 113, No. 5: pp. 1451-1465, 2004.

Lifeform. Nasco. Diagnostic and Procedural Ear Trainer LF01090U Instruction Manual (2009).

Centers for Disease Control and Prevention. Ambulatory Care Use and Physician Visits. Available: http://www.cdc.gov/nchs/fastats/docvisit.htm (Sep. 15, 2012).

D'Eredità, R., Porcine small intestinal submucosa (SIS) myringoplasty in children: A randomized controlled study, Int. J. Pediatr. Otorhinolaryngol. 79: pp. 1085-1089 (2015).

http://www.gtzip.com/helpfaqs.html, Accessed Feb. 12, 2016.

http://www.plastifab.ca/a-upload-pdfs/13_01.pdf, Accessed Feb. 12, 2016.

Krueger, P.S. et al., Vortex Rings in Bio-inspired and Biological Jet Propulsion, Advances in Science and Technology, vol. 58: 237-246 (Sep. 2, 2008).

Shi, L. et al., Biochemical and biomechanical characterization of porcine small intestinal submucosa (SIS): a mini review, Int J Burn Trauma, pp. 2013;3(4): 173-179 (Nov. 15, 2013).

Volandri, G. et al., Biomechanics of the tympanic membrane, Journal of Biomechanics. 44: pp. 1219-1236 (2011).

* cited by examiner

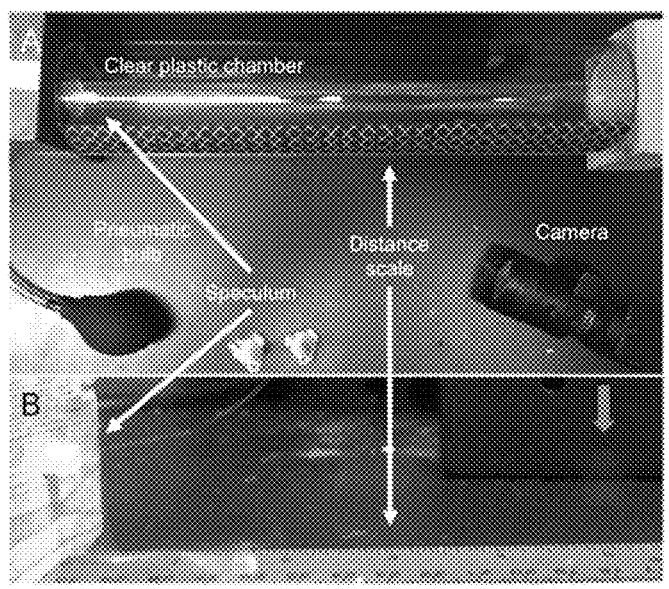
FIG. 11A
FIG. 11B
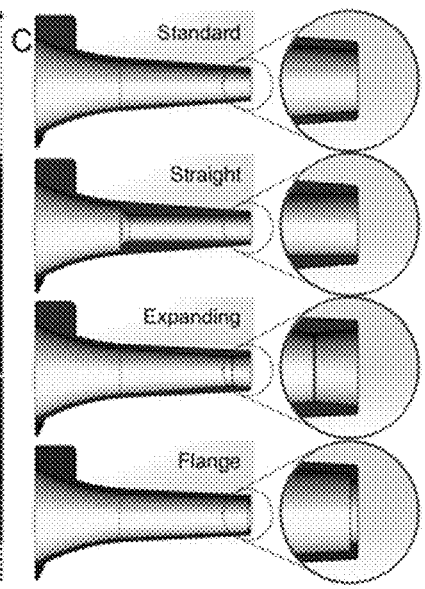
FIG. 11C
FIG. 12A STANDARD
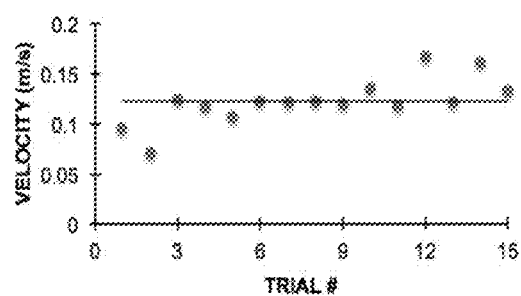
St. Dev. = 0.0231; Range = 0.0964
FIG. 12B STRAIGHT
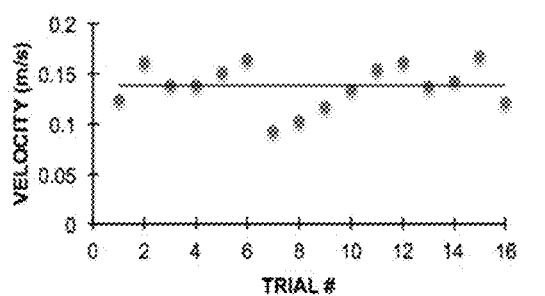
St. Dev. = 0.0219; Range = 0.0743
FIG. 12C EXPANDING
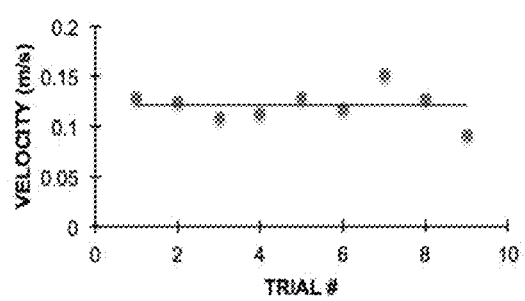
St. Dev. = 0.0167; Range = 0.0602
FIG. 12D FLANGE
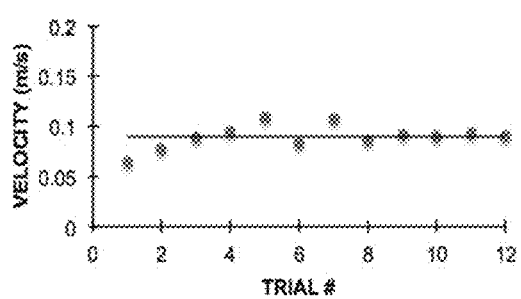
St. Dev. = 0.0119; Range = 0.0445

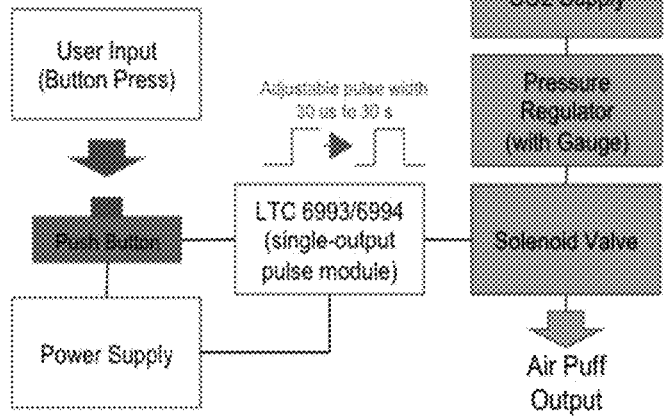
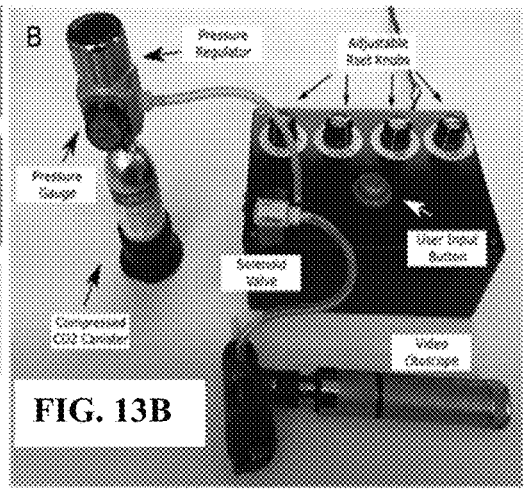
FIG. 13A
FIG. 13B
FIG. 13C
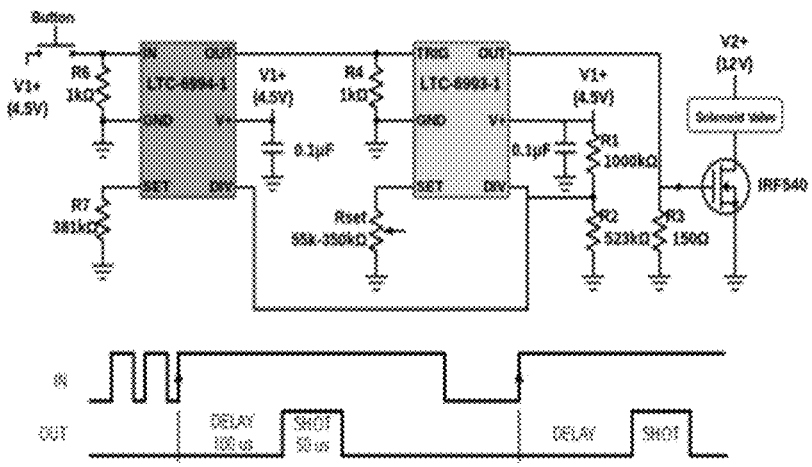
FIG. 14
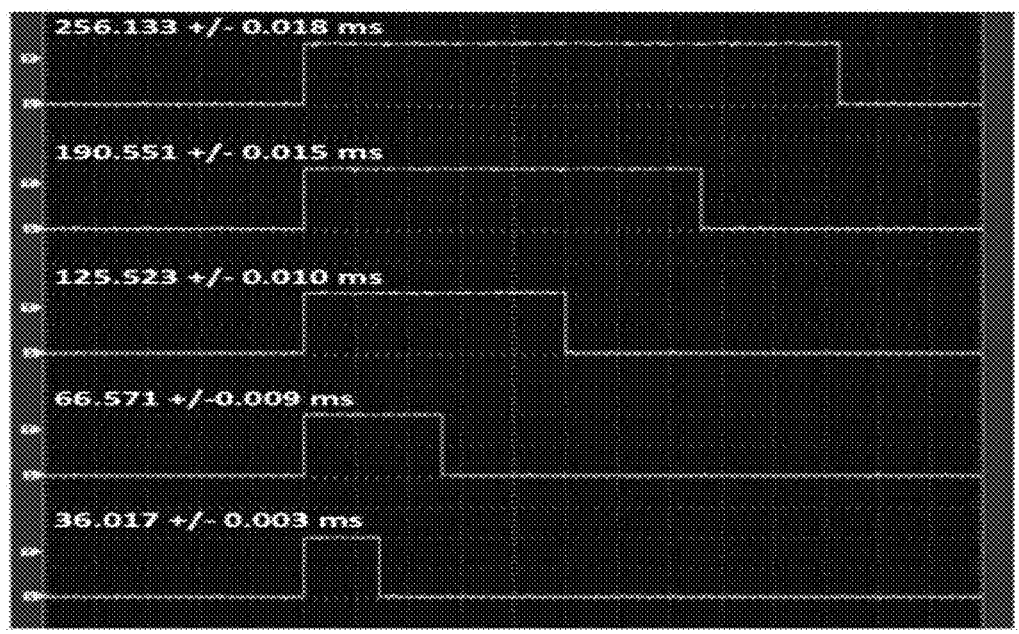

FIG. 15A FLANGE - MANUAL BULB
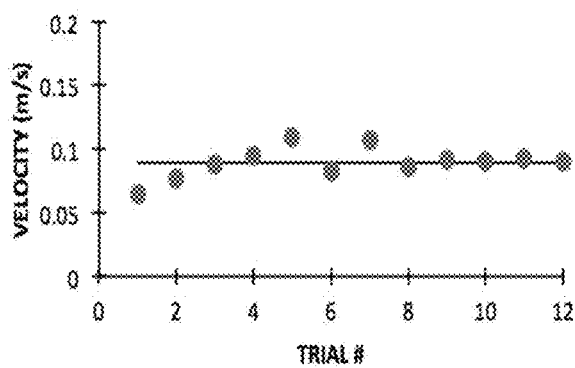
St. Dev. = 0.0119; Range = 0.0445
FIG. 15B FLANGE - AUTOMATED
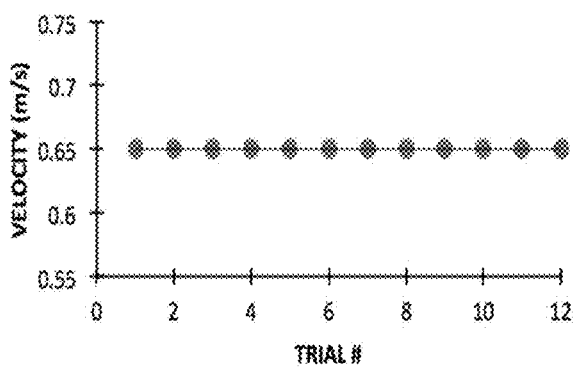
St. Dev./Range = N/A - sub-resolution
FIG. 16A
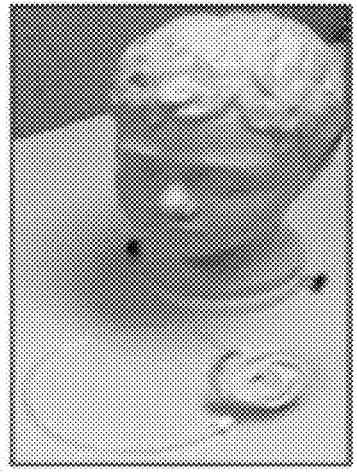
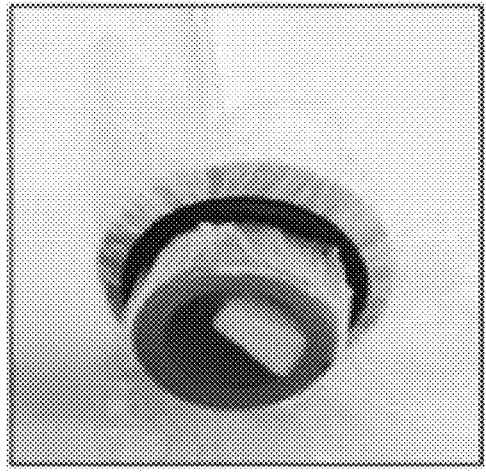
FIG. 16B
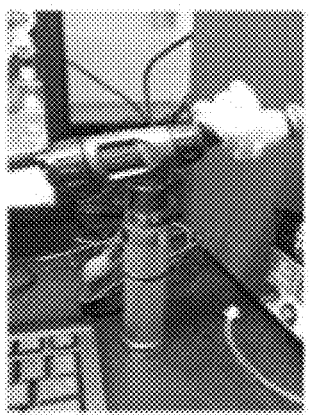
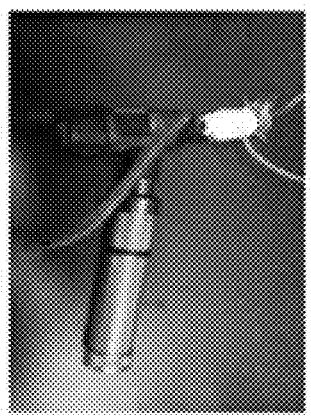

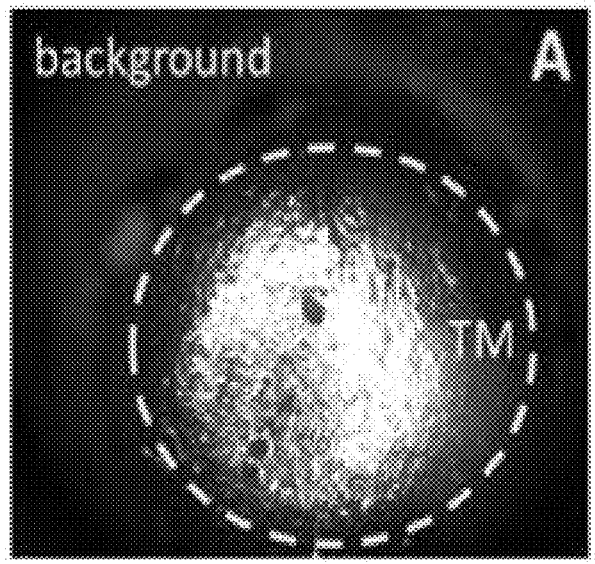
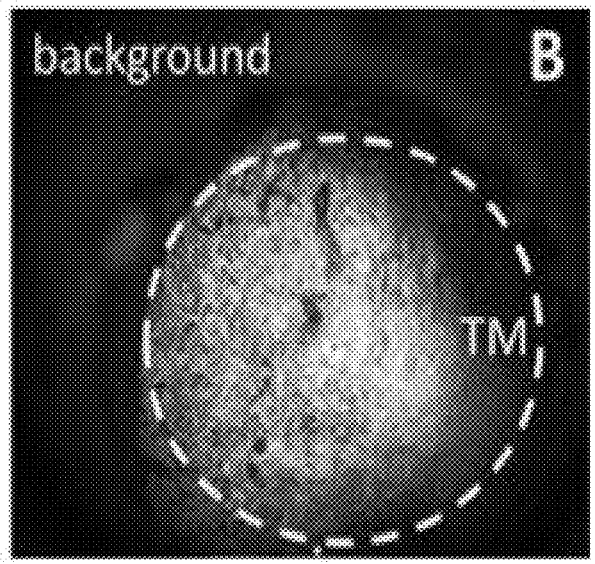
FIG. 17A  FIG. 17B
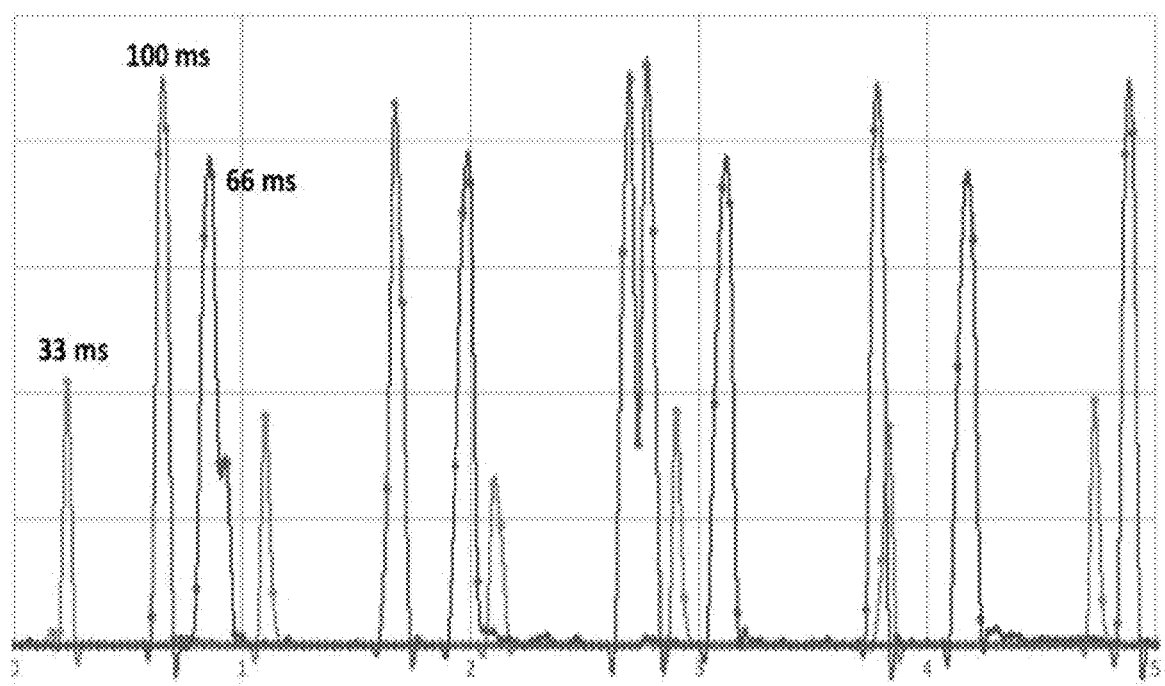
FIG. 18

OTOSCOPE TIP AND METHODS OF USE

CROSS-REFERENCE TO RELATED APPLICATIONS

The present application claims priority to and is a continuation-in-part from U.S. patent application Ser. No. 15/806,653, filed Nov. 8, 2017, which is a continuation from PCT application serial no. PCT/US2016/031450, which is filed May 9, 2016; which claims priority from U.S. provisional application Ser. No. 62/158,765, filed May 8, 2015, all herein incorporated by their entireties.

BACKGROUND

The invention generally relates to the field of otoscopy and in particular to an improved otoscopic tip element for use with otoscopic apparatus.

Ear infections are the leading cause of hearing loss and most common reason for surgery in children. They are responsible for 30M visits to physicians each year in the U.S. and represent a nearly $10B burden on the U.S. economy. The American Academy of Pediatrics (AAP) and the American Academy of Otolaryngology (AAO) recommend pneumatic otoscopy as the gold standard for diagnosing this disease, wherein a change in pressure is delivered to the ear canal to modulate the eardrum; however, very few physicians perform the exam correctly due to difficulty establishing a seal of the ear canal.

The current gold standard for diagnosing middle ear infections is otoscopy, where a lens is used to visually examine the surface of the tympanic membrane (TM), or eardrum. However, this exam is highly subjective, with misdiagnosis rates of up to 50% amongst typical physicians. The addition of pneumatic otoscopy to the standard exam can increase the accuracy of the exam to 90%, and is part of the recommended guidelines developed by the American Academy of Pediatrics (AAP) and the American Academy of Otolaryngology (AAO). Pneumatic otoscopy, or the use of a traditional otoscope supplemented with an insufflation bulb, allows the physician to control the pressure in the ear canal to induce deflections of the TM. A physician then observes the deflection behavior of the TM to deduce the presence or absence of an effusion in the middle ear. However, this additional exam is rarely performed correctly because it is very difficult to obtain a sufficient seal of the ear canal using the current otoscope and speculum technology on the market.

Current disposable specula make it difficult to obtain a seal of the ear canal, and even products designed for pneumatic use perform very poorly due to the use of hard rubber material and non-ideal geometry. Currently, the most commonly used specula are standard tips in 4.2 mm (adult) or 2.7 mm (pediatric) sizes. While these tips are good for interfacing with the ear canal and provide access to a surface image of the TM, they are not designed specifically to facilitate sealing of the ear canal for pneumatic otoscopy. As a result, pneumatic otoscopy is rarely performed and even, more importantly, rarely performed accurately. There have been attempts at pneumatic-specific specula tips, such as the SofSeal and SofSpec from Welch Allyn, but these products do not seal the ear canal significantly better than standard tips, which explain the poor adoption of the SofSeal specula by physicians. The SofSeal uses a hard rubber, which does not seal well with the ear canal.

Correct performance and evaluation of a pneumatic otoscope exam alongside a traditional otoscope exam increases diagnostic accuracy of otitis media (OM) from 50% to better than 90% amongst experienced users, and it is the strongest diagnostic recommendation from AAP and AAO for OM. Despite this strong recommendation from the guideline providers, less than 50% of physicians utilize pneumatic otoscopy as part of their normal patient exam, and 43% of pneumatic otoscope exams are performed or interpreted incorrectly. The biggest reason for the poor adoption and use of this technique is the difficulty associated with obtaining a seal of the ear canal. Sealing the ear canal is currently a requirement to perform pneumatic otoscopy, and it can be very difficult to achieve with current tools and in the presence of uncooperative pediatric patients. The present invention attempts to solve these problems, as well as others.

SUMMARY OF THE INVENTION

Provided herein are systems, methods, and designs of speculum tips for pneumatic otoscopy. A speculum tip is disclosed and generally comprises: a cylindrical configuration including a narrow distal tip region longitudinally extending from a larger proximal region, wherein the distal tip region generates a toroidal vortex throughout a central shaft lumen coaxially disposed within the distal tip region; a distal end of the central shaft lumen includes a distal opening from which the toroidal vortex travels to displace a membrane; the proximal region includes a proximal opening operably coupled with a proximal lumen coaxially disposed within the proximal region as to receive a pulse of fluid.

A method of generating a toroidal vortex for a speculum tip is disclosed and comprises: generating a toroidal vortex through speculum tip comprising a cylindrical configuration with a narrow distal tip region longitudinally extending from a larger proximal region; passing a pulse of fluid through a generally central shaft lumen coaxially disposed within the distal tip region and a distal opening on a distal end of the central shaft lumen; and displacing a membrane by the toroidal vortex exiting the distal opening without the requirement of a pressure seal of the ear canal.

The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

FIG. 11A is a photo of the specula testing chamber for video capture of expelled air puff behavior from both commercial and the speculum tip 100, 200, and 300; FIG. 11B is a photo of FIG. 11A with the brightness and contrast enhanced to better visualize the vortex ring (green arrow) produced by the Vortip specula; FIG. 11C are side views of the speculum tip embodiments tested showing the current standard commercial design, a straight cylinder design 100, an expanding or negative taper design 200, and a flange design 300.

FIGS. 12A-12D are graphs showing the air velocities of the speculum tips in FIG. 11C including the current commercial specula design, the three Vortip designs produced similar air velocities with smaller standard deviation and range. The flange Vortip embodiment 300 produced the most stable and consistent vortex rings compared to the other two Vortip embodiments 100 and 200, which was observed both qualitatively and quantitatively.

FIG. 13A is a block diagram of the automated stimulus module using a compressed air source. Black lines indicate electrical/data connections, blue lines indicate pneumatic/air tubing connections. Light blue blocks indicate the pneumatic components of the module. FIG. 13B is a photo of the working prototype on the lab bench. FIG. 13C is a circuit diagram (top) for the custom circuit for driving the automated stimulus delivery by converting a user press of the trigger button (i.e. IN) into a controlled release from the pressure gauge (i.e. OUT) according to the shown signal trace (bottom).

FIG. 14 is a graph of the Representative oscilloscope traces at 5 pulse durations and these durations were repeatable down to 1-microsecond precision across 20 traces at each pulse duration.

FIGS. 15A-15B are graphs of the compared to (A) the current commercial pneumatic bulb, which requires manual control, the automated stimulus generator performed more precisely, to the point of a sub-resolution standard deviation and range due to the limitations of the detection method used.

FIG. 16A is a photo of the pneumatic deflection experimental setup for the Life/form ear model. The model is comprised of a pediatric sized head, a removable ear, and a middle ear module with removable membrane, o-ring, and pressure-controllable chamber. FIG. 16B are photos from left to right, showing the full ear model, outer ear removed, and middle ear module-only experimental setups.

FIG. 17A is an image of the real-time quantitative analysis of membrane deflection using a simple intensity-based algorithm showing the TM prior to deflection, with background and TM portions of the image annotated. FIG. 17B is an image of the TM during deflection, showing a significant change in intensity. Mean intensity (a.u.) of the rest frame is 131.4, while mean intensity of the deflection frame is 72.15. This provides a simple, real-time method for estimating TM motion.

FIG. 18 is a graph using a simple intensity-based algorithm, TM deflection for three different pulse durations of the automated stimulus module can be easily detected. Such a functionality could be useful to physicians when examining a patient with suspected ear infection with fluid. If fluid has increased the middle ear pressure, the physician will observe a lower peak deflection to confirm the presence of fluid and increased pressure behind the TM.

DETAILED DESCRIPTION OF THE INVENTION

Figure 1A:
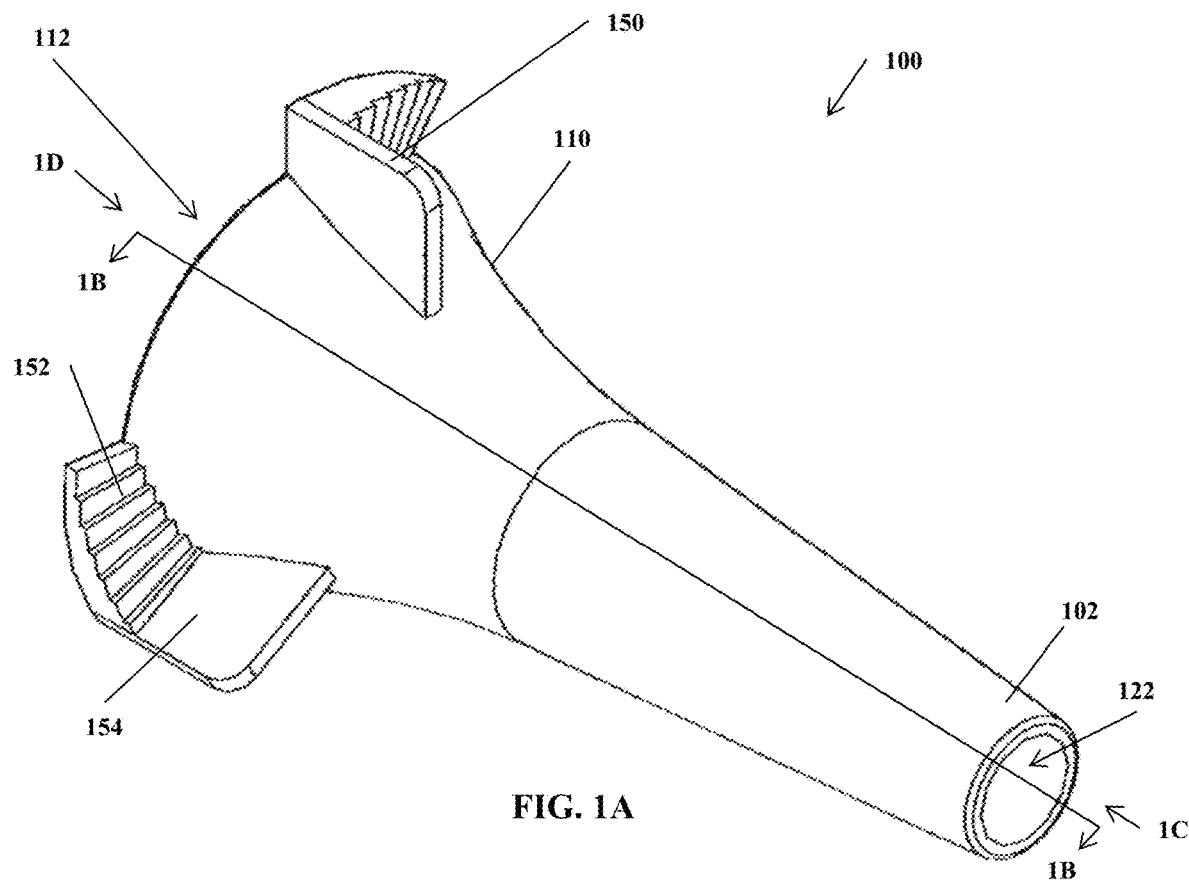
FIG. 1A is a perspective view of one embodiment of the speculum tip.

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant or the patient anatomy to be examined.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant, both in relation to the other endpoint, and independently of the other endpoint.

The use of the terms "a" and "an" and "the" and similar referents in the context of describing the invention are to be construed to cover both the singular and the plural, unless otherwise indicated herein or clearly contradicted by context. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

The speculum tip disclosed herein significantly improves physicians' abilities to efficiently perform this crucial exam. Increasing the use of pneumatic otoscopy will lead to better diagnostic decisions, which will ensure more appropriate prescription of antibiotics and better decisions for surgical intervention. Embodiments of the disposable specula tips used for otoscopy will provide two new features as separate products: (1) enable a quick and easy seal of the ear canal; and (2) deliver the pneumatic insufflation air puff in such a way that a seal of the ear canal is not required. These features will ultimately help the physicians make a more accurate diagnosis and more closely adhere to the AAP and AAO guidelines, resulting in better treatment decisions and less waste.

In one embodiment, a speculum tip is disclosed that allows a quick and easy seal of the ear canal. The speculum tips disclosed herein obviates the need to obtain a seal of the ear canal by delivery of the insufflation stimulus through a specially designed otoscope speculum tip. The speculum tips employ a toroidal vortex fluid to optimize air delivery and facilitate use of pneumatic otoscopy in order to improve compliance with AAP and AAO guidelines for patient care. Alternatively, the speculum tips may incorporate a quick and easy seal of the ear canal by simply inserting the speculum tip into the patient's ear. The speculum tips generate a toroidal vortex to displace the TM, such that physicians can detect changes in TM modulation when making their assessment and diagnosis with the current commercial otoscopy technology. Due to the variation in ear canal and eardrum anatomy, physicians employ different sizes of specula. Small (2.7 mm) diameter speculum tips are used on infants and very young children, while larger (4.2 mm) diameter speculum tips are used on older children and adults. Alternatively, different diameter speculum tips may be provided according to the anatomy of the ear canal or other organ being examined. Alternatively, the speculum tip may be used for other membrane displacement applications, including a tonometer in ophthalmology to displace the eye.

The toroid delivery and dynamic interaction with the eardrum initiates modulation for pneumatic otoscopy. From a thermodynamics view, the toroid vortex can be considered as an impulse or transformation of energy to the eardrum, delivered by the expelled fluid from the distal end of the speculum tip, at which point the interaction with the static air in the ear canal produces the toroid vortex. The impulse energy delivered can be thermodynamically described and related in terms of a pressure or force upon the eardrum to illicit modulation, as shown in EQS. 1-2.

$$\text{Ideal Gas Law: } p = \frac{nRT}{V}; \tag{1}$$

where p is pressure, n is number of moles of gas, R is the gas constant, T is temperature, and V is volume. For our application, n, R, and T remain ambiently constant while V, and consequently p, change upon pneumatic insufflation.

$$\text{Force: pressure relationship: } F = p \times A; \tag{2}$$

where F is the normal force (applied perpendicular to the surface), p is pressure, and A is the surface area. For our application, the A is the surface area of the eardrum to be modulated. This conversion of pressure into force can be used to derive the incident force applied on the eardrum by the toroid vortex.

Impulse (I) is defined as the product of Force (F) times Time (T) for which it is applied. The toroid may include an impulse.

Considering the pneumatic otoscope and ear canal as a thermodynamic system, introduction of pneumatic insufflation impulse through external work, such as volume compression during dynamic impulse delivery, causes an increase in internal energy. In terms of the First Law of Thermodynamics, the energy introduced into the system must be conserved, and thereby introduction of a pneumatic insufflation impulse will result in the modulation of the eardrum (the most pliant of the middle ear tissues), escape through lossy leaks where a seal of the canal is not achieved, or varying degrees of both. Due to inherent difficulty in obtaining a perfect seal of the ear canal, the speculum tip circumvents the need for a seal by delivering a more specialized pneumatic insufflation impulse that will retain more of the initial impulse energy delivered by the user until interaction with the eardrum occurs.

Figure 1B:
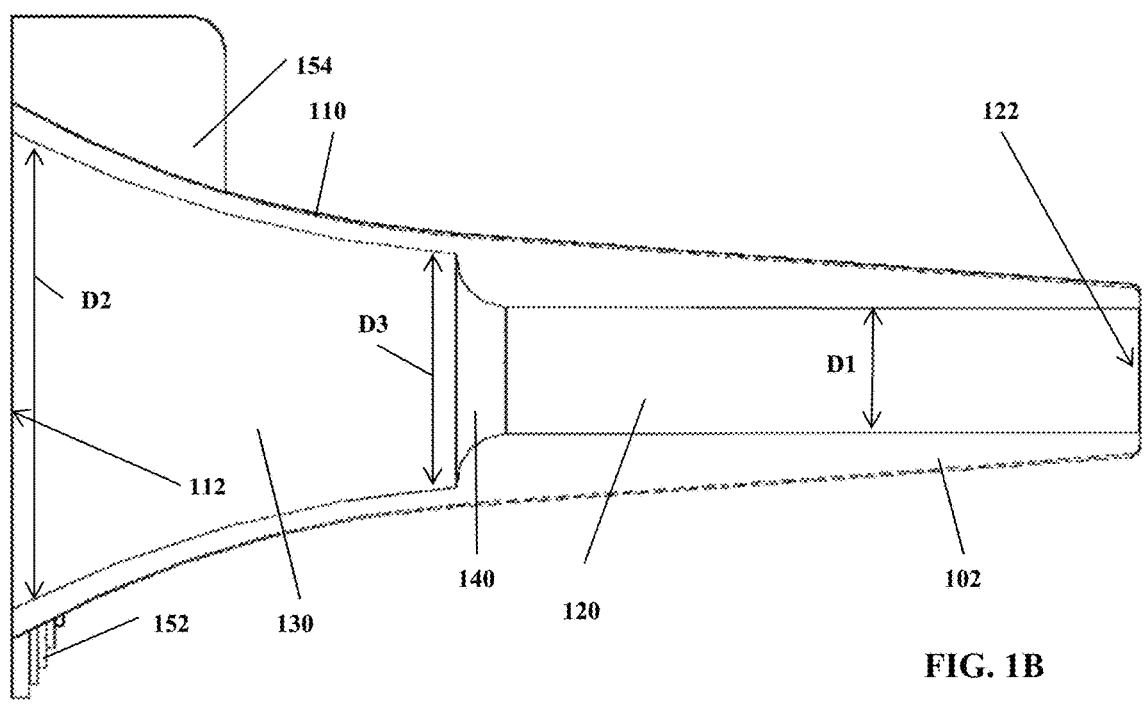
FIG. 1B is a cross-sectional view of one embodiment of the speculum tip taken along line 1B-1B from FIG. 1A.
Figure 1C:
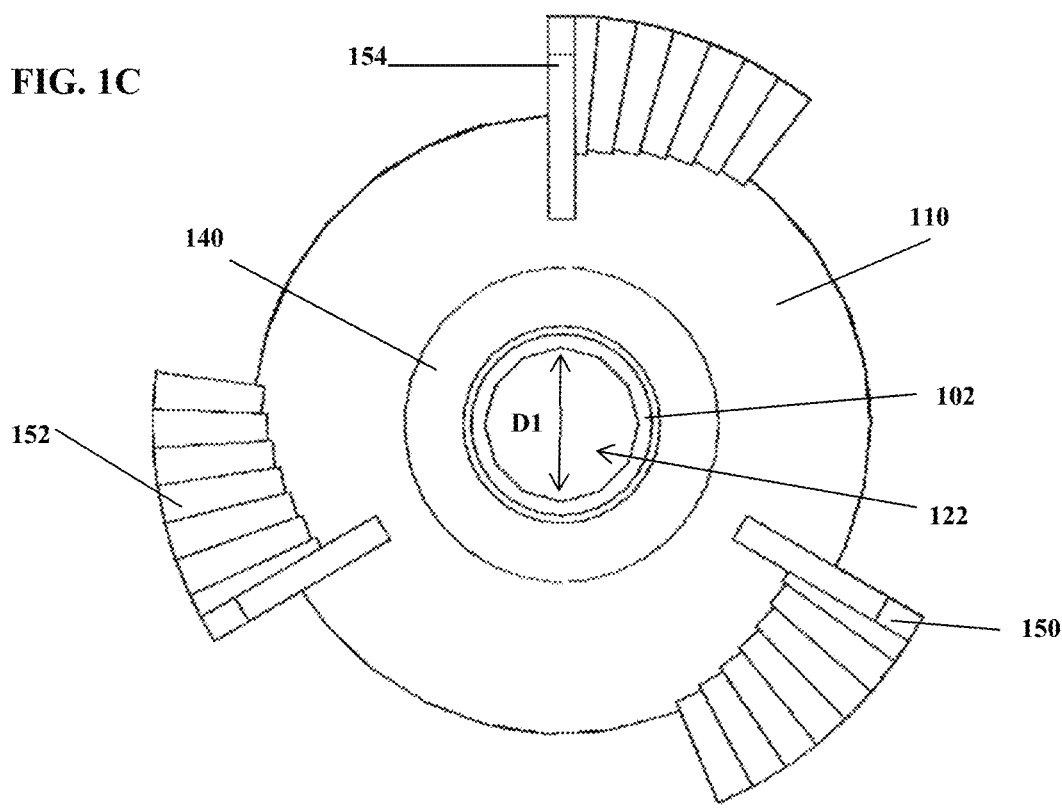
FIG. 1C is a front view of one embodiment of the speculum tip taken from view 1C from FIG. 1A.

Generally speaking, one embodiment of the speculum tip 100 is shown in FIGS. 1A-1D. The speculum tip 100 includes a generally conical configuration with a narrow distal tip region 102 longitudinally extending from a larger proximal region 110. The distal tip region 102 generates a toroidal vortex throughout a generally central shaft lumen 120 coaxially disposed within the distal tip region 102, as shown in FIG. 1B-1C. The distal end of the central shaft lumen 120 includes a distal opening 122 through which the toroidal vortex sufficiently displaces the eardrum without the requirement of a pressure seal of the ear canal. The proximal region 110 includes a proximal opening 112 operably coupled with a proximal lumen 130 disposed within the proximal region 110. The proximal lumen 130 includes a conical or a cylindrical cross-section or profile that narrows to a middle lumen 140, whereby the middle lumen 140 transitions to the central shaft lumen 120. The speculum tip 100 includes a plurality of flanges 150 surrounding the proximal end of the proximal region 110. The flanges 150 include a stepped portion 152 descending from the vertical lip 154. The flanges 150 are used to secure the speculum tip to an otoscope, as to provide the user a grip-like structure to twist or rotate the speculum tip 100 about its longitudinal axis. The flanges 150 may be removed from the speculum tip 100 depending on the otoscope features for securement.

Figure 1D:
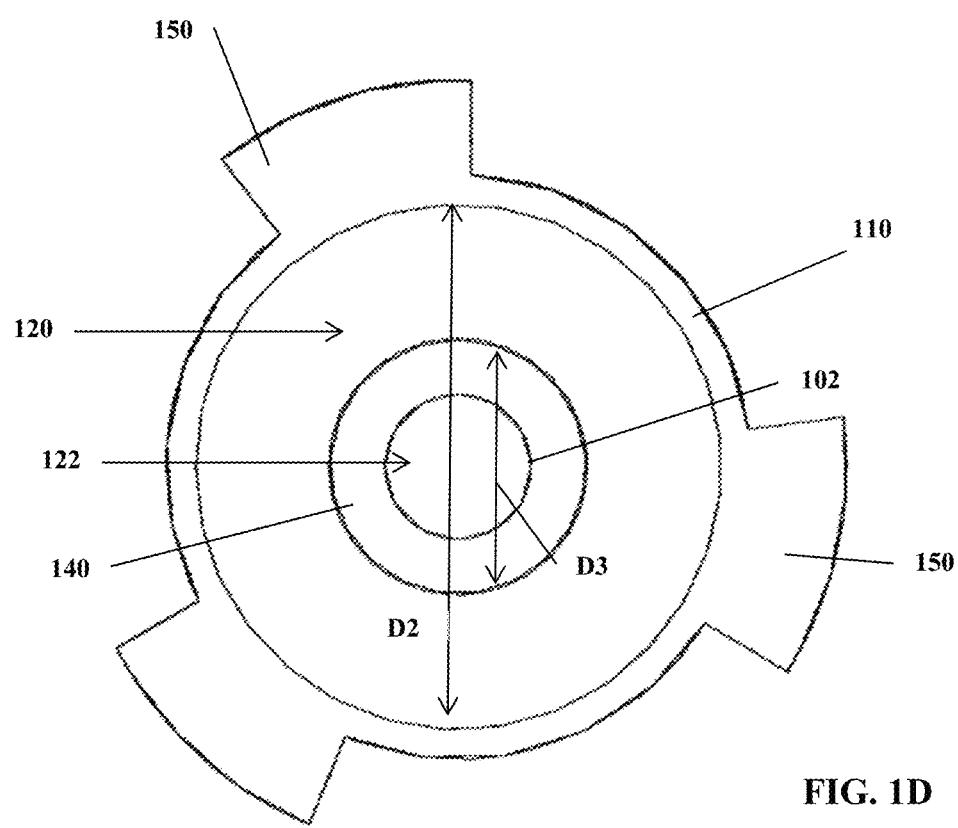
FIG. 1D is a back view of one embodiment of the speculum tip taken from view 1D from FIG. 1A.

In one embodiment, the walls of the central shaft lumen 120 are separated by about 0.1 to about 15 mm as to create the air vortex rings exiting the distal opening 122. As such, the central shaft lumen 120 includes a diameter D1, as shown in FIGS. 1B-1D. The diameter D1 produces a medium-sized toroidal vortex or a constant toroidal vortex, as indicated below. The proximal lumen 130 includes a proximal end with a diameter of D2 and the proximal lumen 130 includes a distal end with a diameter of D3. The diameter D2 is larger or greater than the diameter D3, such that the proximal lumen 130 includes a generally curved cross-section shape or profile. The middle lumen 140 includes a proximal end that substantially aligns with the distal end of the proximal lumen 110. The middle lumen 140 includes a distal end that substantially aligns with the proximal end of the central shaft lumen 120. The toroidal vortex is generated by fluid passing through the proximal lumen 130, traversing the middle lumen 140, and exiting the central shaft lumen 120. In one embodiment, the diameter D2 is formatted as to fit a pneumatic otoscope. In one embodiment, the shaft lumen 120 includes a length sufficient and a bolus of injected air to generate the toroidal vortex, as indicated below. The pneumatic otoscope may be operably coupled to a pressure generator to generate the pulse of fluid within the speculum tip. The pressure generator can be manual, automated, and the like. In one embodiment, the pressure generator is a pump, a bulb, or other method of fluid displacement.

Figure 2A:
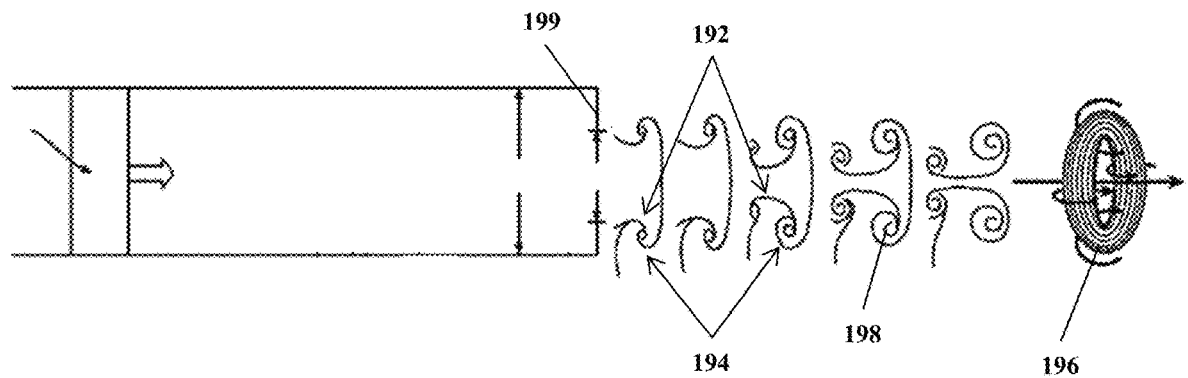
FIG. 2A is a schematic side view of one embodiment of the toroidal vortex.
Figure 2B:
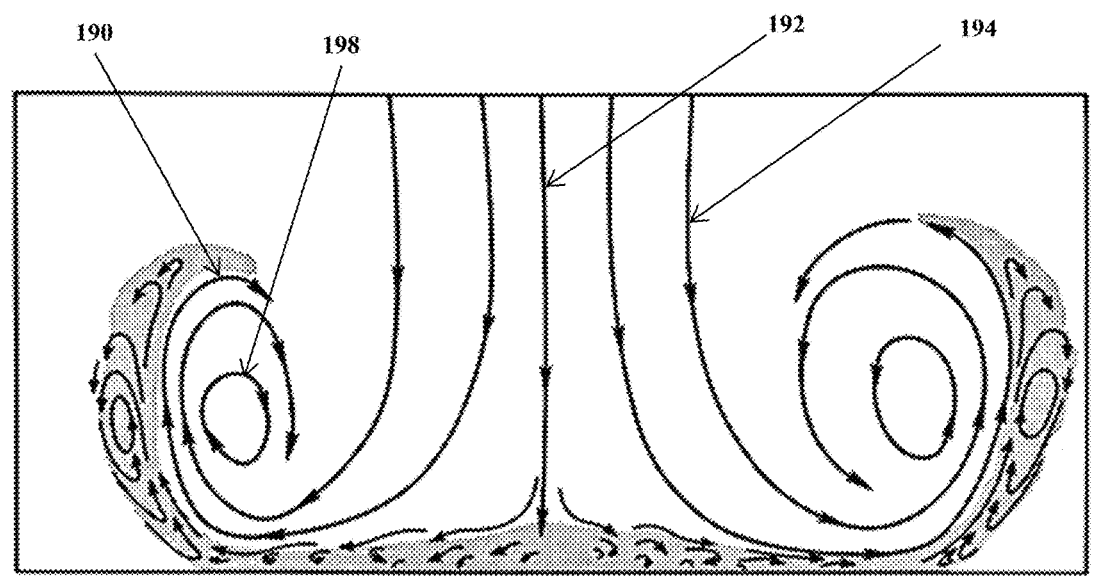
FIG. 2B is a schematic side view of one embodiment of the toroidal vortex.
Figure 2C:
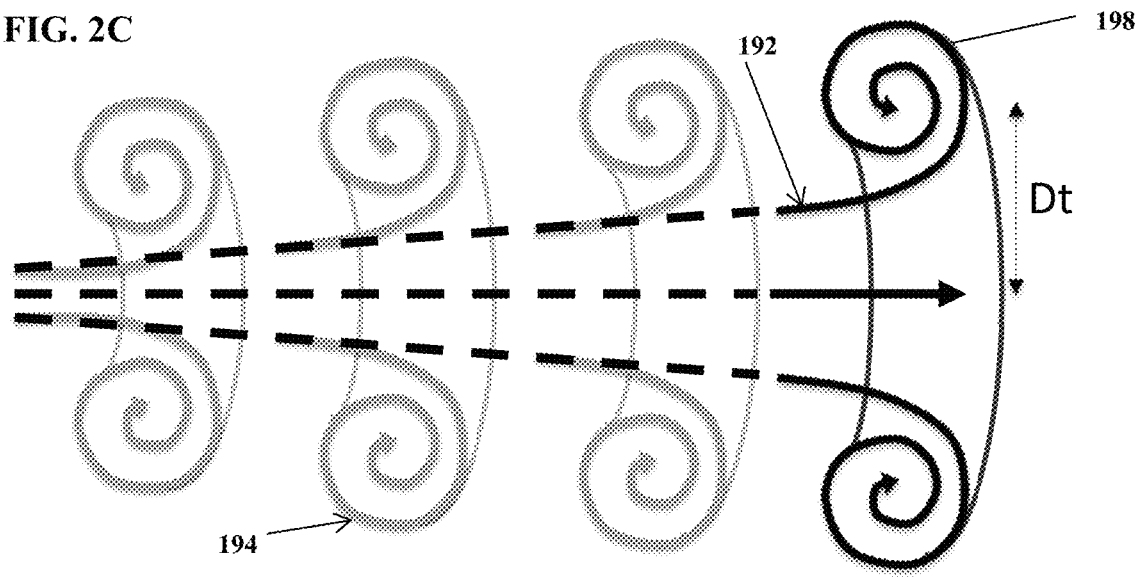
FIG. 2C is a schematic side view of an expanding toroidal vortex.
Figure 2D:
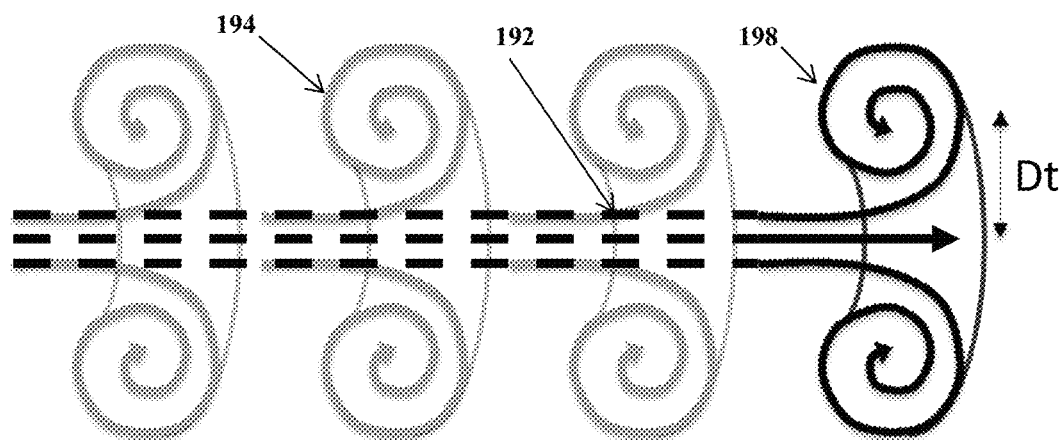
FIG. 2D is a schematic side view of a constant diameter toroidal vortex.
Figure 2E:
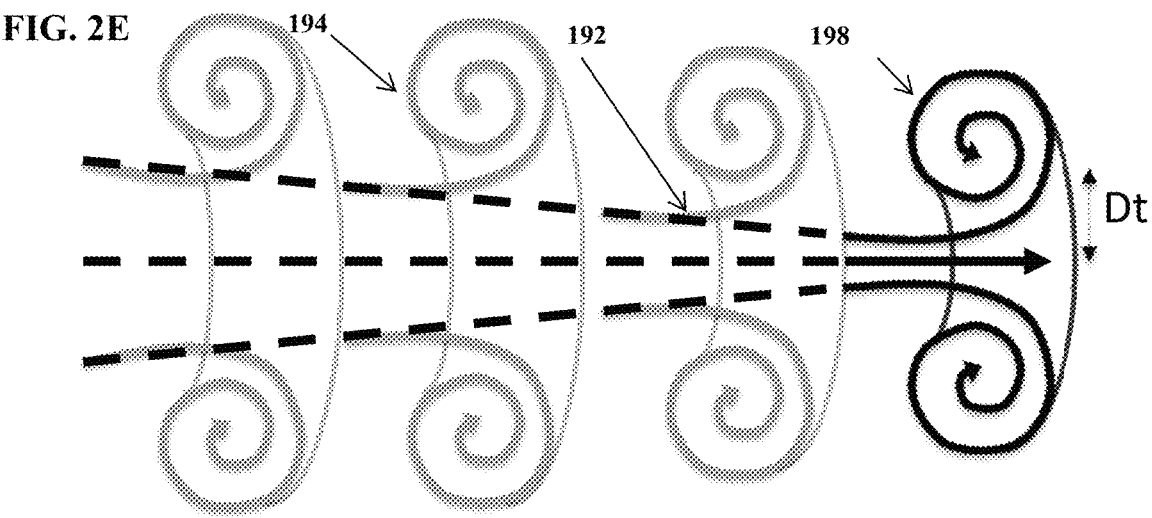
FIG. 2E is a schematic side view of a focusing toroidal vortex.

For the toroidal vortex, a fluid (either air or liquid) is expelled in such a way that a torus-shaped vortex 196 is created out of the central shaft lumen and exiting the distal opening, because the inner edge 192 of the ring 196 moves faster than the outer edge 194, as shown in FIGS. 2A-2B. This vortex ring 196 travels in a perpendicular direction to the plane of the ring, allowing it to carry the spinning fluid 198 and travel much further than simple expulsion (see FIG. 2B). This vortex ring 196 displaces the eardrum without a need to seal the canal due to the more specialized and less lossy impulse pressure/force exerted by the vortex ring structure 196. Several designs disclosed herein may be used to generate toroidal vortices, as shown in the several embodiments of the speculum tips. FIGS. 2A-2B show two toroid vortex examples. These examples require a compact mass of fluid to interact with an interface (e.g. air, liquid, flat solid surface) where one is moving much faster relative to the other. In the most prevalent case, as shown in FIG. 2A, a stationary air or liquid environment interface at the distal end of the toroid-generating device 199 causes drag on the outer edge of the expelled, quick, compact fluid mass, which slows down the outer layers of the fluid mass relative to its core. This aerodynamic drag causes the ejected air to begin rotating. When the slower outer layers slip around and collect at the rear, they re-enter the fluid mass in the wake of the faster moving core and form the toroid ring structure. This ring structure is held together by inward pressure because the air inside the toroid ring is moving faster and, according to Bernoulli's law, is lower pressure than the air on the outside. However, the aerodynamic drag eventually overcomes the energy stored in the toroid ring and the ring dissipates. In another case, as shown in FIG. 2B, toroidal vortices can be formed (as in microbursts) when the compact fluid mass collides with a flat stationary wall. When the compact fluid mass hits the wall, the fluid shoots out radially along the wall plane. The toroidal vortex ring is then produced by the viscous friction between the faster layer of outward flow at the wall's surface and the slower fluid mass in its wake. The toroidal vortex utilizes the drag from an interface not perpendicular to the travel of the vortex (FIG. 2A) and generates an initial compact fluid mass with either a highly pressurized source or stretching and releasing an elastic membrane or spring to create an impulse. In one embodiment, the toroidal vortex includes a fluid burst of at least about 5 mmHg to about 100 mmHg. The fluid burst to create this toroidal vortex may be higher than about 5 mmHg to about 100 mmHg. In one embodiment, the toroidal vortex creates a pressure ring of at least about 5 mmHg to about 75 mmHg to displace the TM and analysis of the response is utilized to diagnosis otitis media. In one embodiment, the pressure ring is about 25 mmHg, and the detected motion of the TM may be at least about 5 mmHg, which may be detected by Optical Coherence Tomography (OCT), as further explained below. The toroidal vortex may be an expanding toroidal vortex, whereby the diameter Dt of the toroidal vortex expands as it travels further away from the speculum tip, as shown in FIG. 2C. The toroidal vortex may be a focusing toroidal vortex that may focus the toroidal vortex to a smaller target, as shown in FIG. 2E. Or the toroidal vortex may be a constant toroidal vortex that maintains the same diameter as it travels away from the speculum tip, as shown in FIG. 2D. The toroidal vortex may be a double-concentric toroidal vortex, which is a double-curling air vortex ring. The diameter of the toroidal vortex may be between about 0.5 to about 8.0 mm.

If the pressure is between about 5 mmHg-100 mmHg and the area is about 50 mm$^2$, then by using equation (2) p=F/A=>F=pA=(0.6666 kPa–13.333 kPa)*5 e−5 m$^2$=33.3 mN–666.6 mN. Thus, the force of the toroidal vortex may be between about 33.3 mN to about 666.6 mN.

The pressure in the sealed ear canal is slowly changed to observe deflection of the TM, because of the sealed canal, this deflection rate is directly tied to and identical to that of the bulb compression/expansion in the user/physician's hand or other air pressure source. In the embodiments disclosed herein, dynamically loading the TM by the toroidal vortex abruptly pushes the TM, which is detected. The rate for the change in pressure may be between about 35 to about 50 milliseconds, in one embodiment. Dynamically loading the TM is abruptly impacting the TM with finite, discrete pulses/vortices of gas (air, $CO_2$, etc.), which load the TM over a much smaller time scale than current pneumatic otoscopy technique.

Figure 3A:
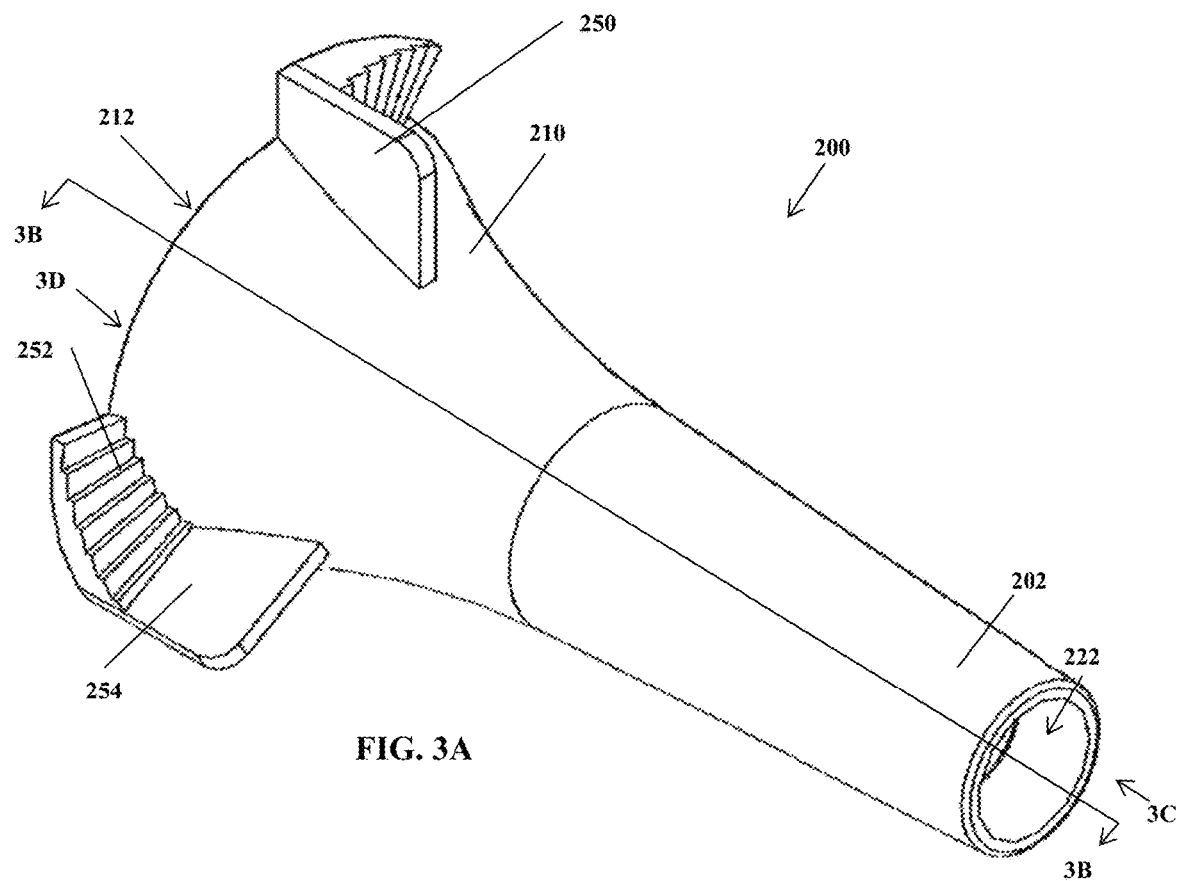
FIG. 3A is a perspective view of one embodiment of the speculum tip.
Figure 3B:
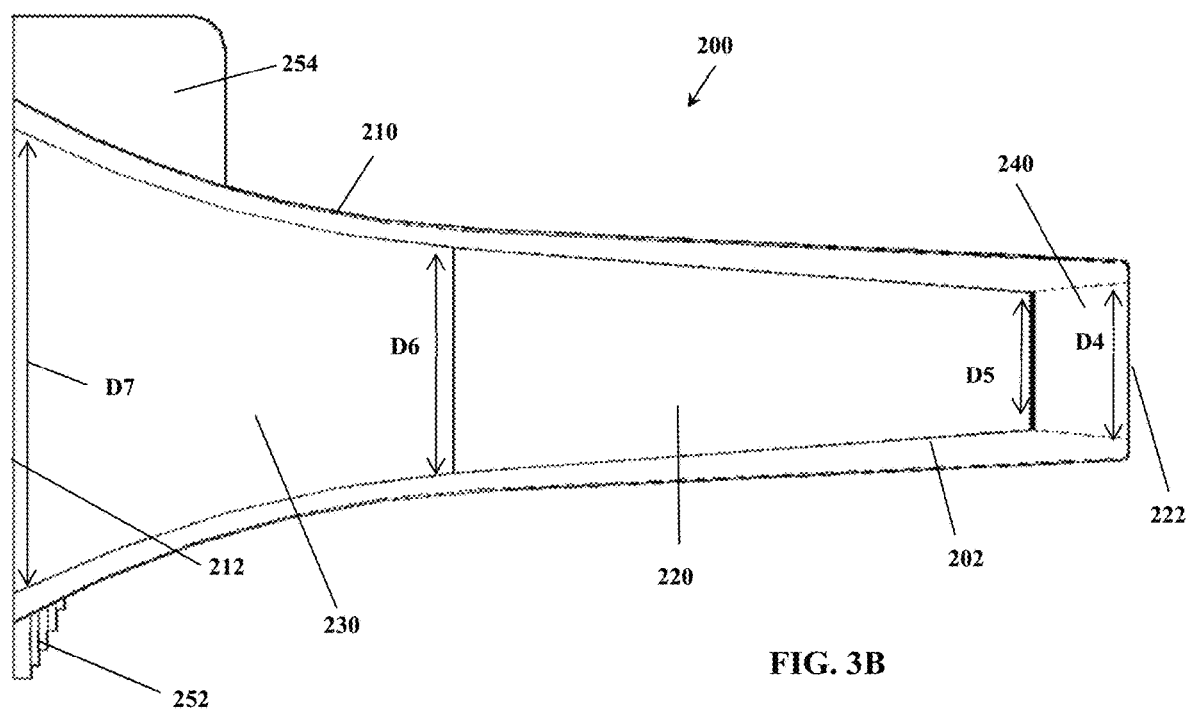
FIG. 3B is a cross-sectional view of one embodiment of the speculum tip taken along line 3B-3B from FIG. 3A.
Figure 3C:
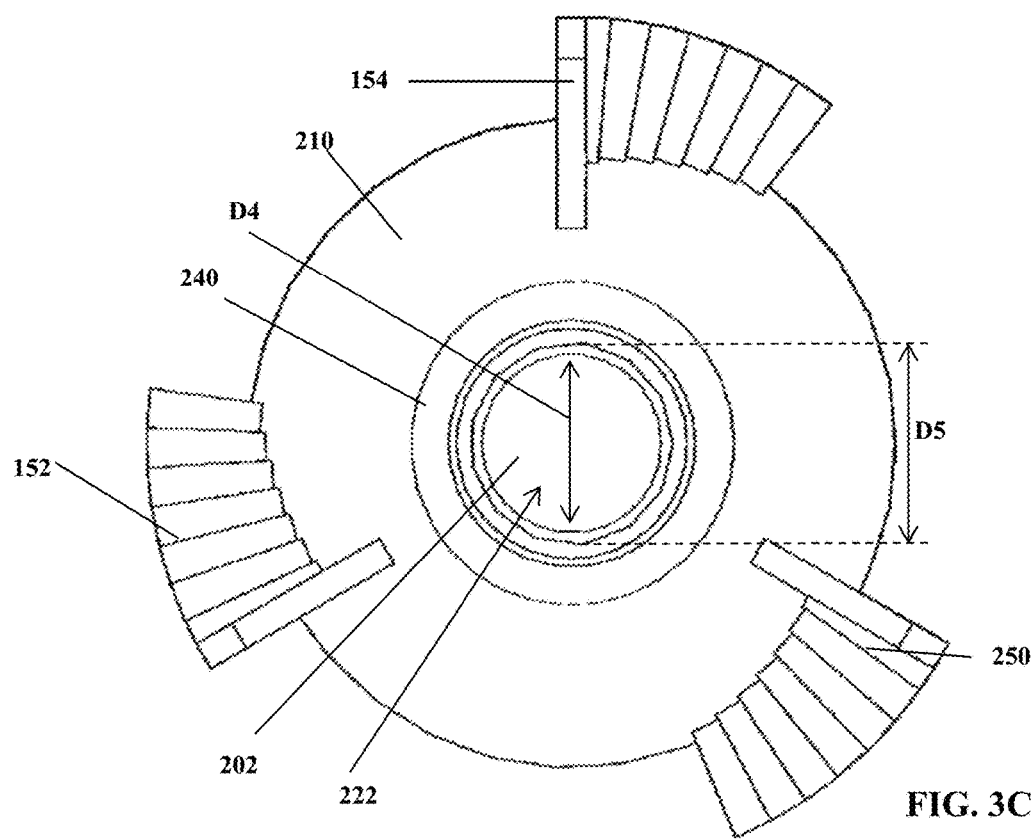
FIG. 3C is a front view of one embodiment of the speculum tip taken from view 3C from FIG. 3A.

Another embodiment of the speculum tip 200 is shown in FIGS. 3A-3D. Similar features and elements are present in the speculum tip 200 as the speculum tip 100 with several slight variations. The speculum tip 200 includes a generally conical configuration with a narrow distal tip region 202 longitudinally extending from a larger proximal region 210. The distal tip region 202 generates a toroidal vortex by fluid traversing through a central shaft lumen 220 and a distal lumen 240 coaxially disposed within the distal tip region 202, as shown in FIG. 3B-3C. The distal end of the central shaft lumen 220 includes a distal end that is coupled to a proximal end of the distal lumen 240. The central shaft lumen 220 includes a conical cross-section or profile that narrows to the distal lumen 240. The distal lumen 240 includes trapezoidal cross-section or profile that includes a distal end larger than a proximal end. The distal end of the distal lumen 240 includes a distal opening 222 through which the toroidal vortex displaces the eardrum without the requirement of a pressure seal of the ear canal. The proximal region 210 includes a proximal opening 212 operably coupled with a proximal lumen 230 disposed within the proximal region 210. The proximal lumen 230 includes a conical cross-section or profile that narrows to the central shaft lumen 220, whereby the central shaft lumen 220 transitions to the distal lumen 240. The speculum tip 200 includes a plurality of flanges 250 surrounding the proximal end of the proximal region 210. The flanges 250 include a stepped portion 252 descending from the vertical lip 254. The flanges 250 are used to secure the speculum tip to an otoscope as to provide the user a grip-like structure to twist or rotate the speculum tip 100 about its longitudinal axis. The flanges 150 may be removed from the speculum tip 100 depending on the otoscope features for securement.

Figure 3D:
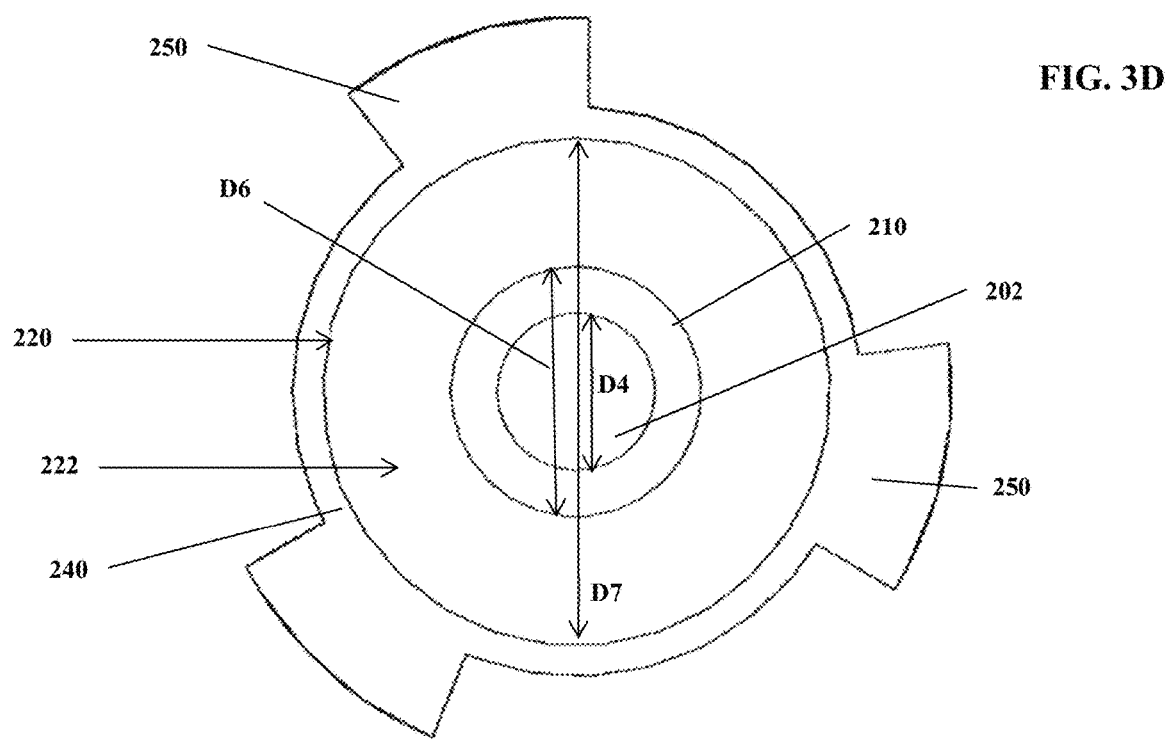
FIG. 3D is a back view of one embodiment of the speculum tip taken from view 3D from FIG. 3A.

In one embodiment, the walls of the central shaft lumen 220 are separated by about 0.5 to about 15 mm as to create the air vortex rings exiting the distal opening 222. The distal lumen 240 includes an expanded tip cross-section or profile, where the distal end of the distal lumen 240 includes a diameter D4 that produces a large-sized or expanding toroidal vortex as indicated previously as shown in FIGS. 3B-3D. As such, the distal end of the central shaft lumen 220 narrows to a diameter D5, wherein the distal end of the central shaft lumen 220 coaxially aligns with the proximal end of the distal lumen 240. The narrowing of the central shaft lumen 220 to diameter D5 causes the vortex diameter to expand rather than maintain the diameter as it travels distally. The diameter D4 is larger than the diameter D5 to produce a large-sized or expanding toroidal vortex through the distal opening 222, after which the toroid ring diameter expands as it travels forward or away from the distal opening 222.

The proximal lumen 230 includes a distal end with a diameter D6 that coaxially aligns with the proximal end of the central shaft lumen 220, as shown in FIGS. 3B-3D. The diameter D6 is larger or greater than the diameter D5 of the distal end of the central shaft lumen 220, such that the central shaft lumen 220 includes a generally trapezoidal cross-section or profile. The proximal lumen 230 includes a proximal end with a diameter of D7. The diameter D7 is larger or greater than the diameter D6 of the distal end of the proximal lumen 230, such that the proximal lumen 230 includes a generally curved cross-section shape or profile. The toroidal vortex is generated by fluid passing through the proximal lumen 230, traversing the central shaft lumen 220, and exiting the distal lumen 220 and distal opening 222.

Figure 4A:
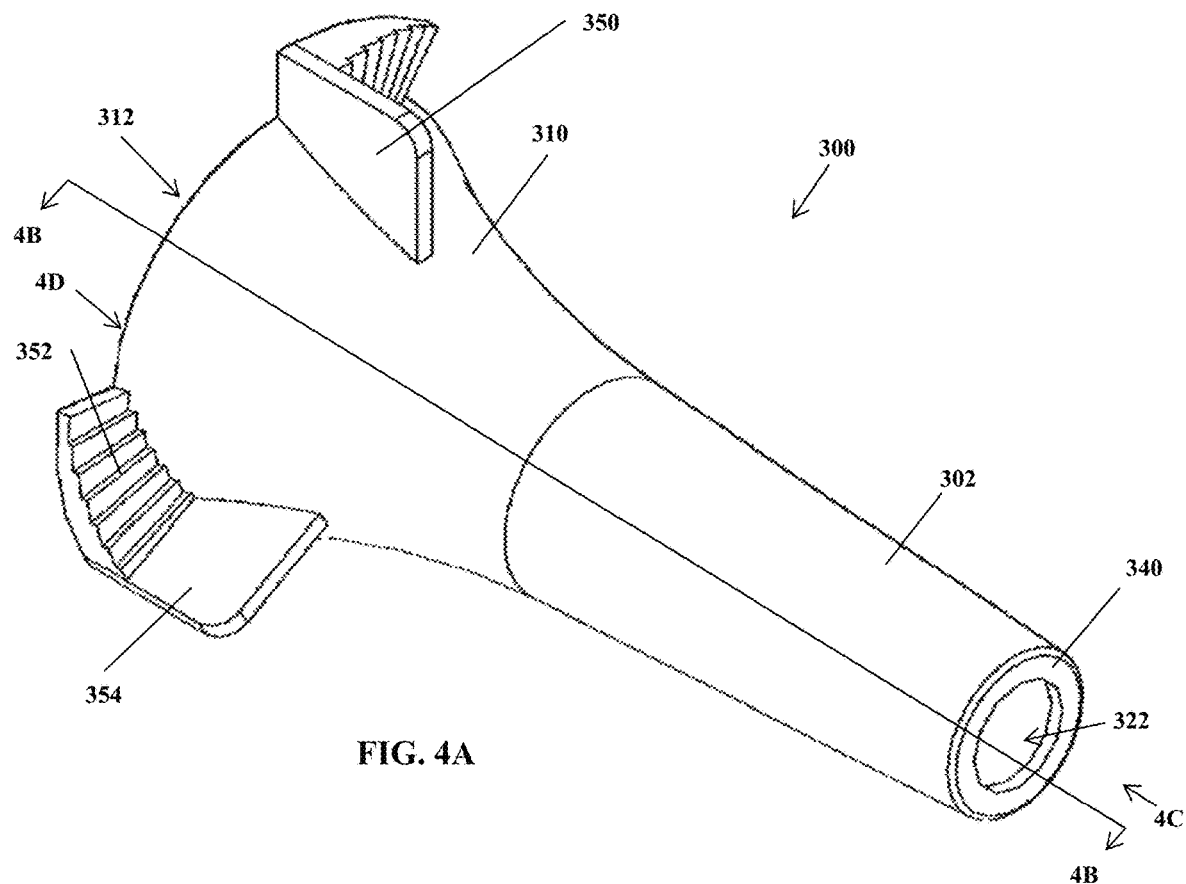
FIG. 4A is a perspective view of one embodiment of the speculum tip.
Figure 4B:
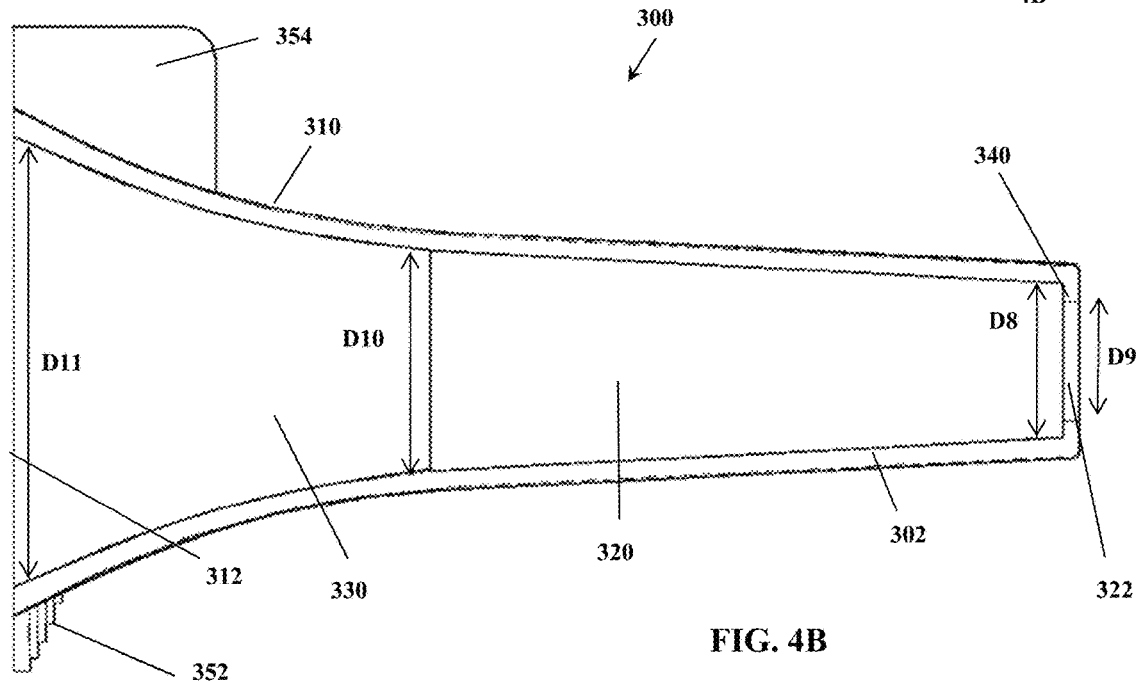
FIG. 4B is a cross-sectional view of one embodiment of the speculum tip taken along line 4B-4B from FIG. 4A.
Figure 4C:
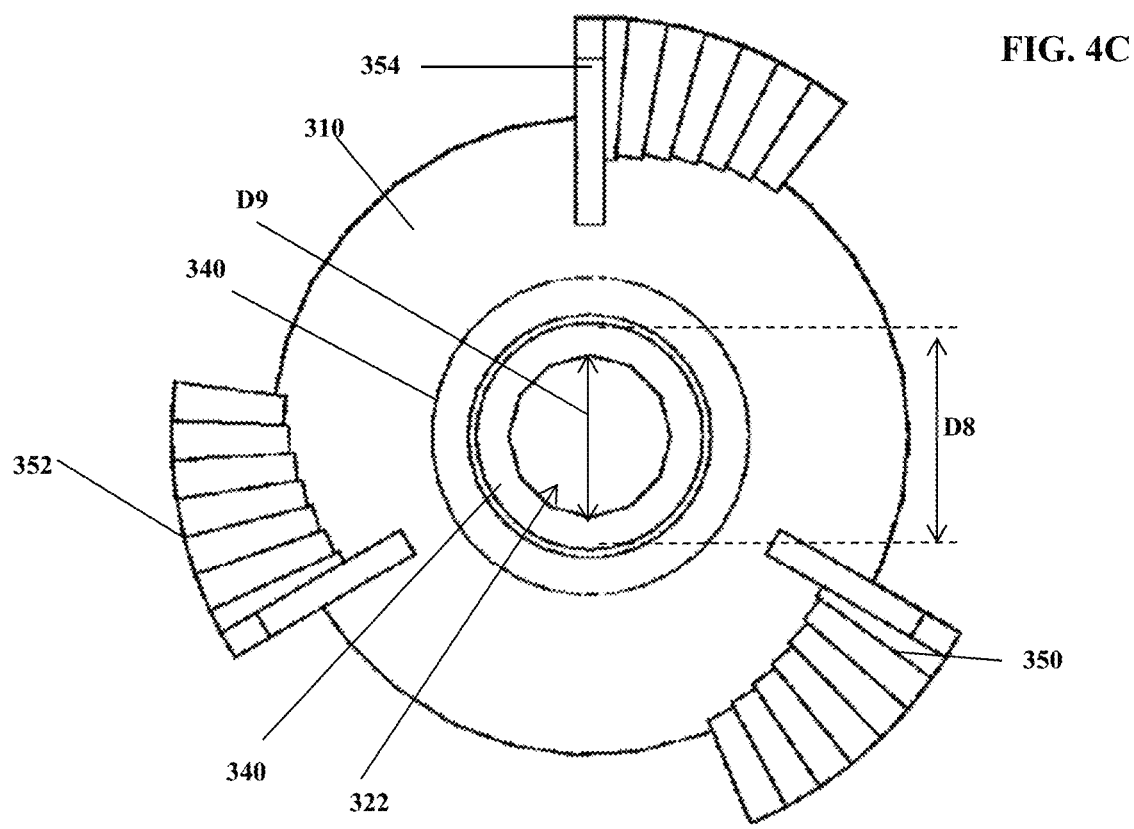
FIG. 4C is a front view of one embodiment of the speculum tip taken from view 4C from FIG. 4A.

Another embodiment of the speculum tip 300 is shown in FIGS. 4A-4D. Similar features and elements are present in the speculum tip 300 as in the speculum tips 100 and 200 with several slight variations. The speculum tip 300 includes a generally conical configuration with a narrow distal tip region 302 longitudinally extending from a larger proximal region 310. The distal tip region 302 generates a toroidal vortex by fluid traversing through a central shaft lumen 320 and a distal lumen lip 340 coaxially disposed within the distal tip region 302, as shown in FIG. 4B-4C. The distal end of the central shaft lumen 320 includes a distal lip 340 that surrounds a distal opening 322 as to create a smaller distal opening 322 compared to the distal end of the central shaft lumen 320. The central shaft lumen 320 includes a conical cross-section or profile that narrows to the distal opening 322. The central shaft lumen 320 includes trapezoidal cross-section or profile that includes a distal end larger than a proximal end. The distal opening 322 through which a constant toroidal vortex or focusing toroidal vortex displaces the eardrum without the requirement of a pressure seal of the ear canal. The proximal region 310 includes a proximal opening 312 operably coupled with a proximal lumen 330 disposed within the proximal region 310. The proximal lumen 330 includes a conical cross-section or profile that narrows to the central shaft lumen 320. The speculum tip 300 includes a plurality of flanges 350 surrounding the proximal end of the proximal region 310. The flanges 350 include a stepped portion 352 descending from the vertical lip 354. The flanges 350 are used to secure the speculum tip to an otoscope as to provide the user a grip-like structure to twist or rotate the speculum tip 100 about its longitudinal axis. The flanges 150 may be removed from the speculum tip 100 depending on the otoscope features for securement.

Figure 4D:
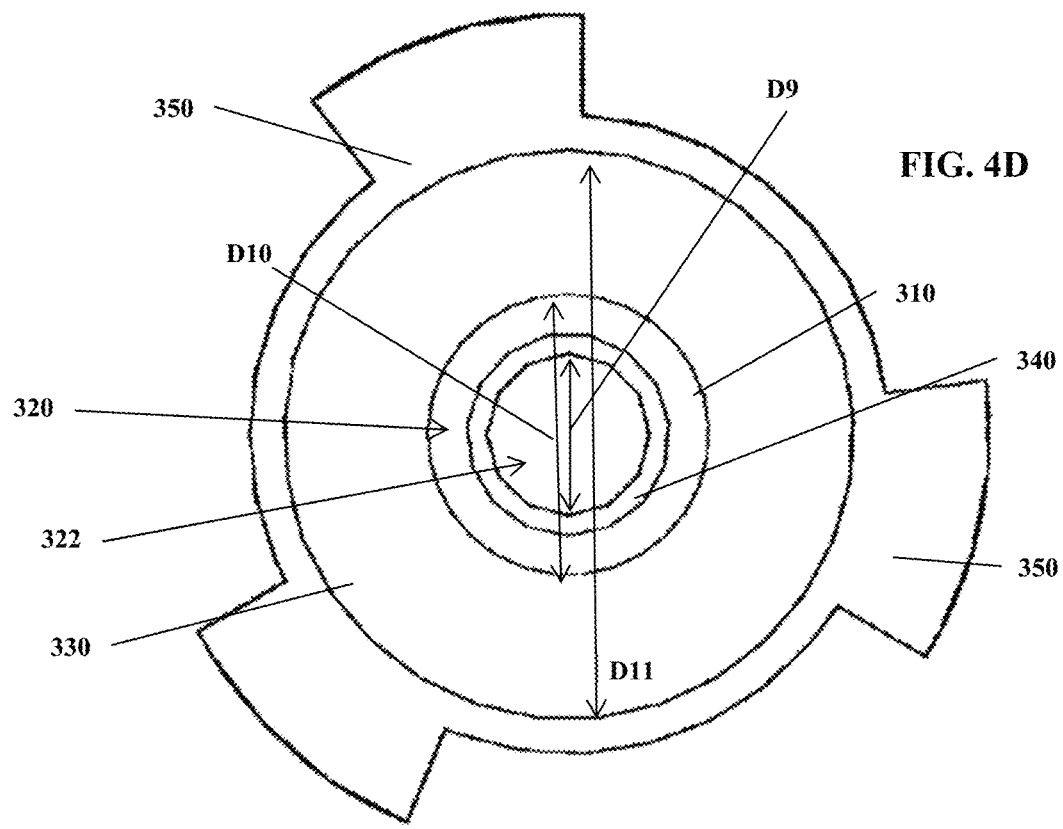
FIG. 4D is a back view of one embodiment of the speculum tip taken from view 4D from FIG. 4A.

In one embodiment, the walls of the central shaft lumen 320 are separated by about 0.1 to about 15 mm as to create the air vortex rings exiting the distal opening 322. The central shaft lumen 320 includes a diameter D8 that is narrowed by the distal end of the central shaft lumen 320, as shown in FIGS. 4B-4D. The distal lip 340 includes a diameter D9 that creates a smaller distal opening 322 than the diameter D8 of the distal end of the central shaft lumen 320, which produces a smaller diameter vortex ring. As such, the diameter D9 is smaller than the diameter D8. In one embodiment, an optimum ratio of D9 and D8 is: $D9=D8/2$. In other embodiments, the ration of D9 to D8 is between about $D9=D8/4$ to about $D9=5(D8)/6$.

The proximal lumen 330 includes a distal end with a diameter D10 that coaxially aligns with the proximal end of the central shaft lumen 320, as shown in FIG. 4B. The diameter D10 is larger or greater than the diameter D8 of the distal end of the central shaft lumen 320, such that the central shaft lumen 320 includes a generally trapezoidal cross-section or profile. The proximal lumen 330 includes a proximal end with a diameter of D11. The diameter D11 is larger or greater than the diameter D10 of the distal end of the proximal lumen 330, such that the proximal lumen 330 includes a generally curved cross-section shape or profile. A focusing toroidal vortex is generated by fluid passing through the proximal lumen 330, traversing the central shaft lumen 320, and exiting the distal opening 322.

Figure 5A:
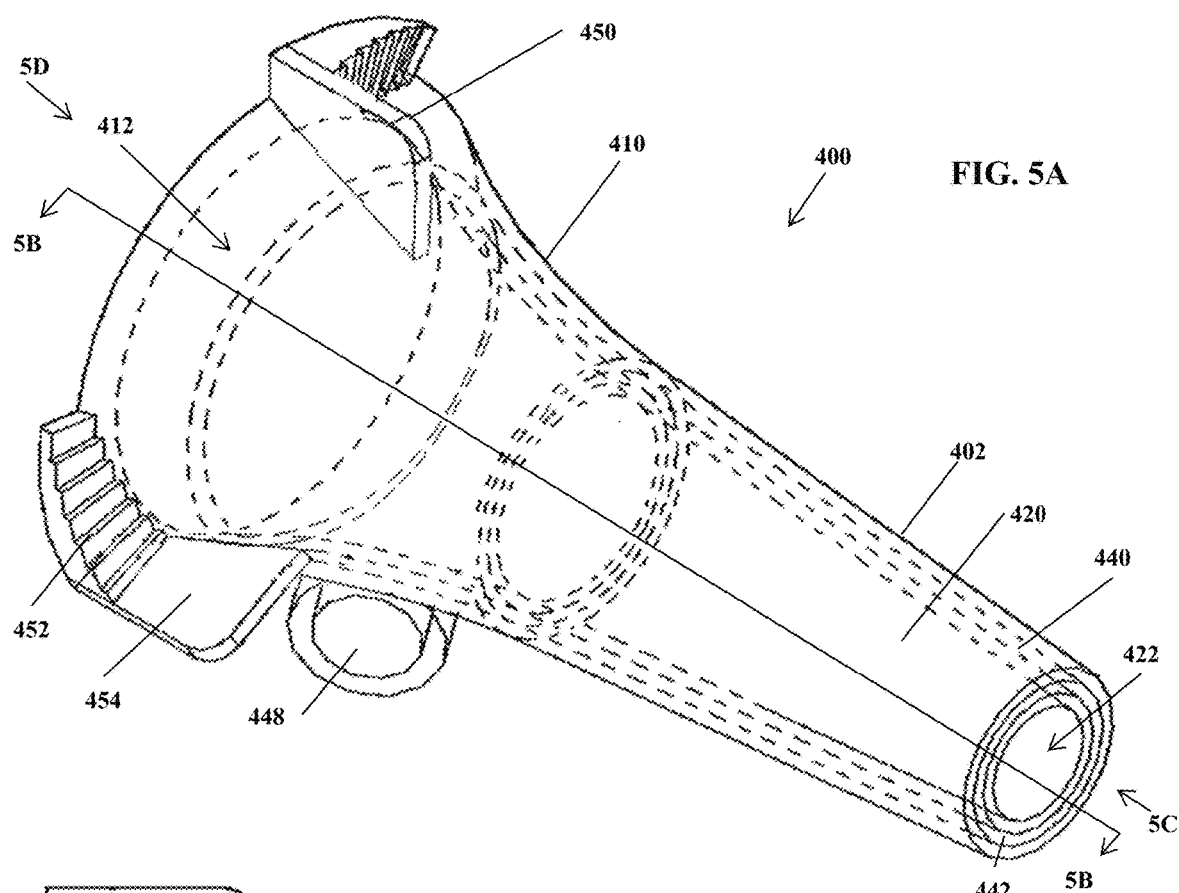
FIG. 5A is a perspective view of one embodiment of the speculum tip.
Figure 5B:
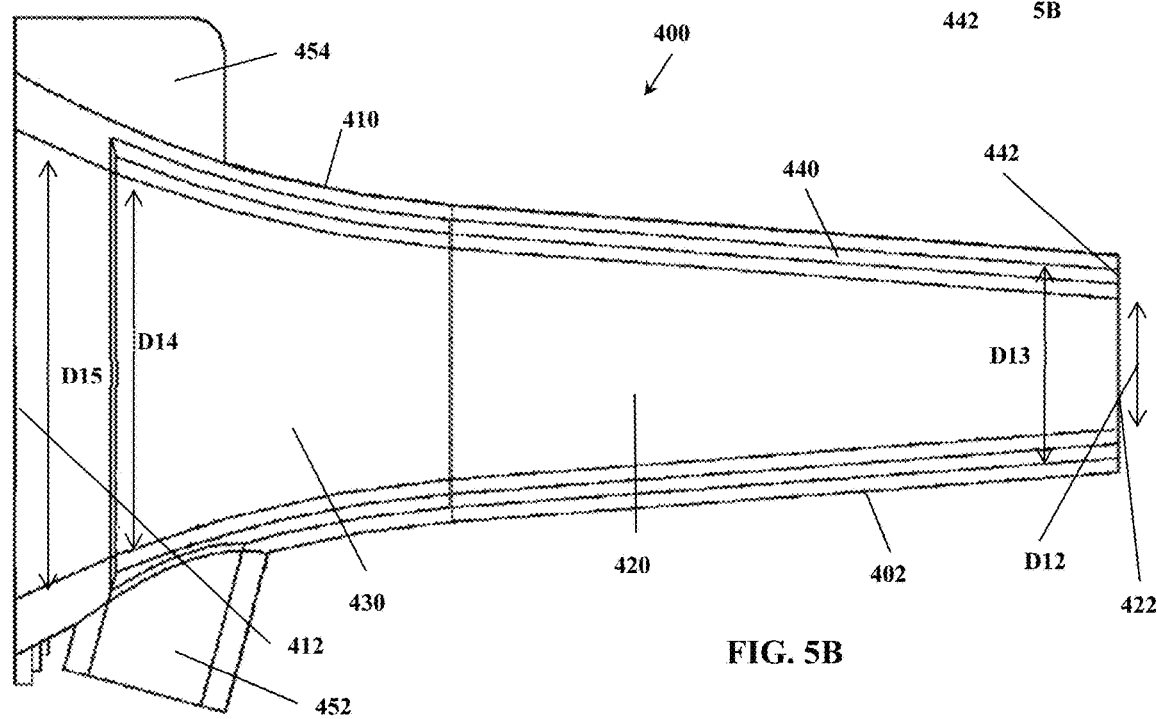
FIG. 5B is a cross-sectional view of one embodiment of the speculum tip taken along line 5B-5B from FIG. 5A.
Figure 5C:
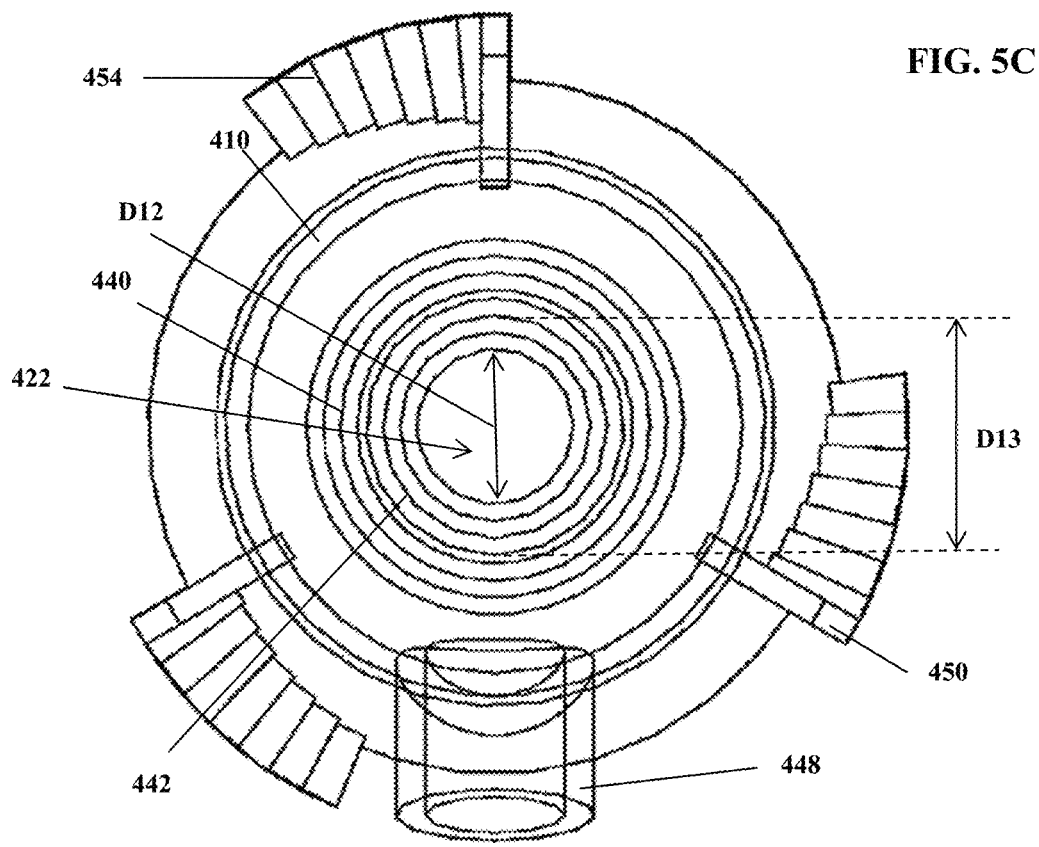
FIG. 5C is a front view of one embodiment of the speculum tip taken from view 5C from FIG. 5A.

Another embodiment of the speculum tip 400 is shown in FIGS. 5A-5D. Similar features and elements are present in the speculum tip 400 as in the speculum tips 100-300 with several slight variations. The speculum tip 400 includes a generally conical configuration with a narrow distal tip region 402 longitudinally extending from a larger proximal region 410. The distal tip region 402 includes a coaxially disposed central shaft lumen 420. The proximal region 410 includes a proximal lumen 430. A second outer lumen 440 coaxially surrounds the central shaft lumen 420 and the proximal lumen 430 and extends from a portion of the proximal region 410. The outer lumen 440 generates a double-concentric toroidal vortex by fluid traversing through the outer lumen 440, as shown in FIG. 5B-5C. The distal end of the central shaft lumen 420 includes a distal opening 422 and the distal end of the second outer lumen 440 includes a distal outer opening 442. The central shaft lumen 420 and the proximal lumen 430 include a conical cross-section or profile that narrows to the distal opening 422. The second outer lumen 440 is fluidly coupled with an outer port 448 disposed on the exterior surface of the proximal region 410. The distal outer opening 442 generates a toroidal vortex that displaces the eardrum without the requirement of a pressure seal of the ear canal. The distal outer opening 442 generates a greater impulse and evenly distributed impulse, and the different toroid shape due to the ring outlet will displace the tympanic membrane for a stronger and safer modulation. The proximal region 410 includes a proximal opening 412 operably coupled with the proximal lumen 430 coaxially disposed within the proximal region 410. The proximal lumen 430 includes a conical cross-section or profile that narrows to the central shaft lumen 420. The second outer lumen 440 includes a second proximal opening 442 fluidly coupled with the proximal lumen 430. The second outer lumen 440 includes conical cross-section or profile that narrows to the distal outer opening 442. The speculum tip 400 includes a plurality of flanges 450 surrounding the proximal end of the proximal region 410. The flanges 450 include a stepped portion 452 descending from the vertical lip 454. The flanges 450 are used to secure the speculum tip to an otoscope as to provide the user a grip-like structure to twist or rotate the speculum tip 100 about its longitudinal axis. The flanges 150 may be removed from the speculum tip 100 depending on the otoscope features for securement.

Figure 5D:
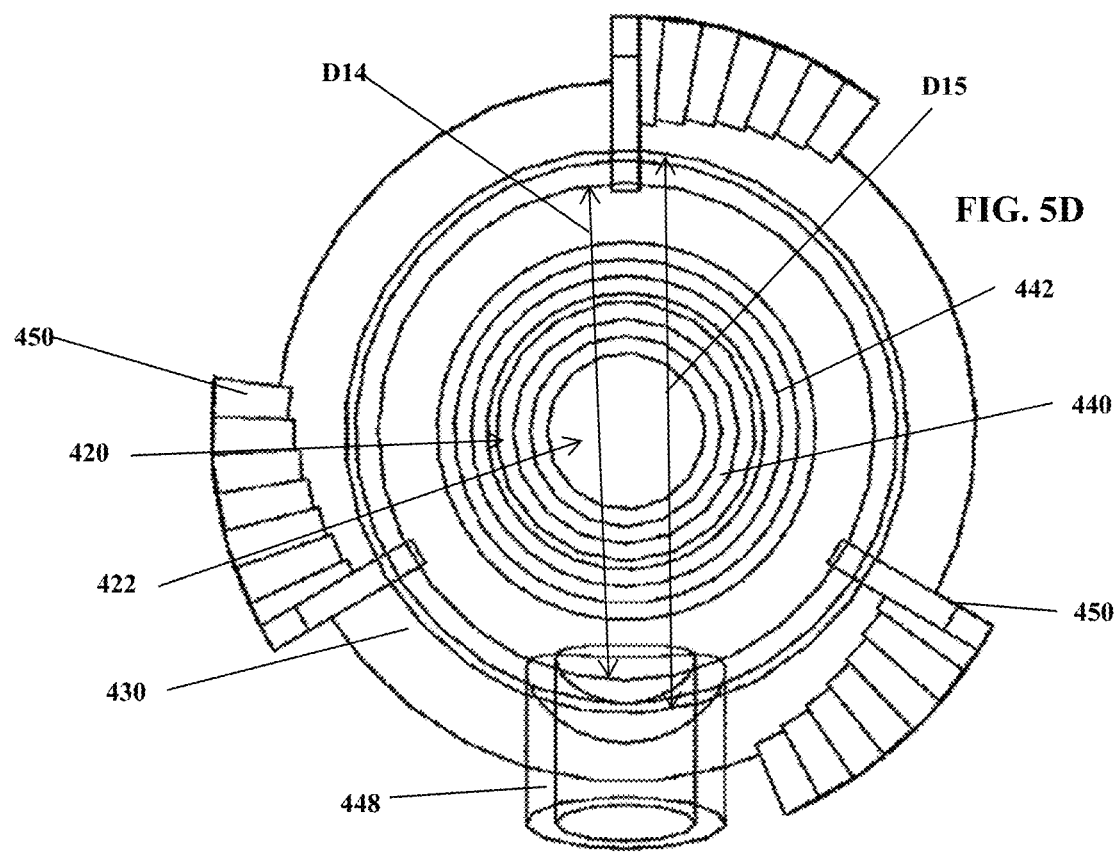
FIG. 5D is a back view of one embodiment of the speculum tip taken from view 5D from FIG. 5A.

In one embodiment, the walls of the central shaft lumen 420 are separated by about 0.1 to about 15 mm as to create the double-curling air vortex ring exiting the distal outer opening 442. The central shaft lumen 420 includes a diameter D13 that is narrowed by the distal end of the central shaft lumen 420, as shown in FIGS. 5B-5D. The distal outer opening 442 includes a diameter D12 that creates a larger circular opening than the diameter D13 of the distal end of the central shaft lumen 420, as to produce a double-curling air vortex ring. As such, the diameter D12 is smaller than the diameter D13.

The proximal lumen 430 includes a distal end with a diameter D15 that coaxially aligns with the proximal end of the central shaft lumen 420, as shown in FIG. 5B. The diameter D15 is larger or greater than the diameter D13 of the distal end of the central shaft lumen 420, such that the central shaft lumen 420 includes a generally trapezoidal cross-section or profile. The second outer lumen 440 includes a proximal outer opening 442 with a diameter of D14. The diameter D14 is larger or greater than the diameter D12 of the distal end of the second outer lumen 440, such that the second outer lumen 440 includes a generally curved cross-section shape or profile. D12 includes a diameter to allow for sufficient field-of-view for imaging and also D12 includes a diameter that is structurally sound to interface and administer the pneumatic pulse without structural issues/failure. The double-curling toroidal vortex is generated by fluid passing through the inlet 452, traversing the second outer lumen 440, and exiting the distal outer opening 442. The drag forces from the inner and outer diameter surfaces along the second outer lumen 440 cause the double-curling behavior of the toroidal vortex.

Figure 6A:
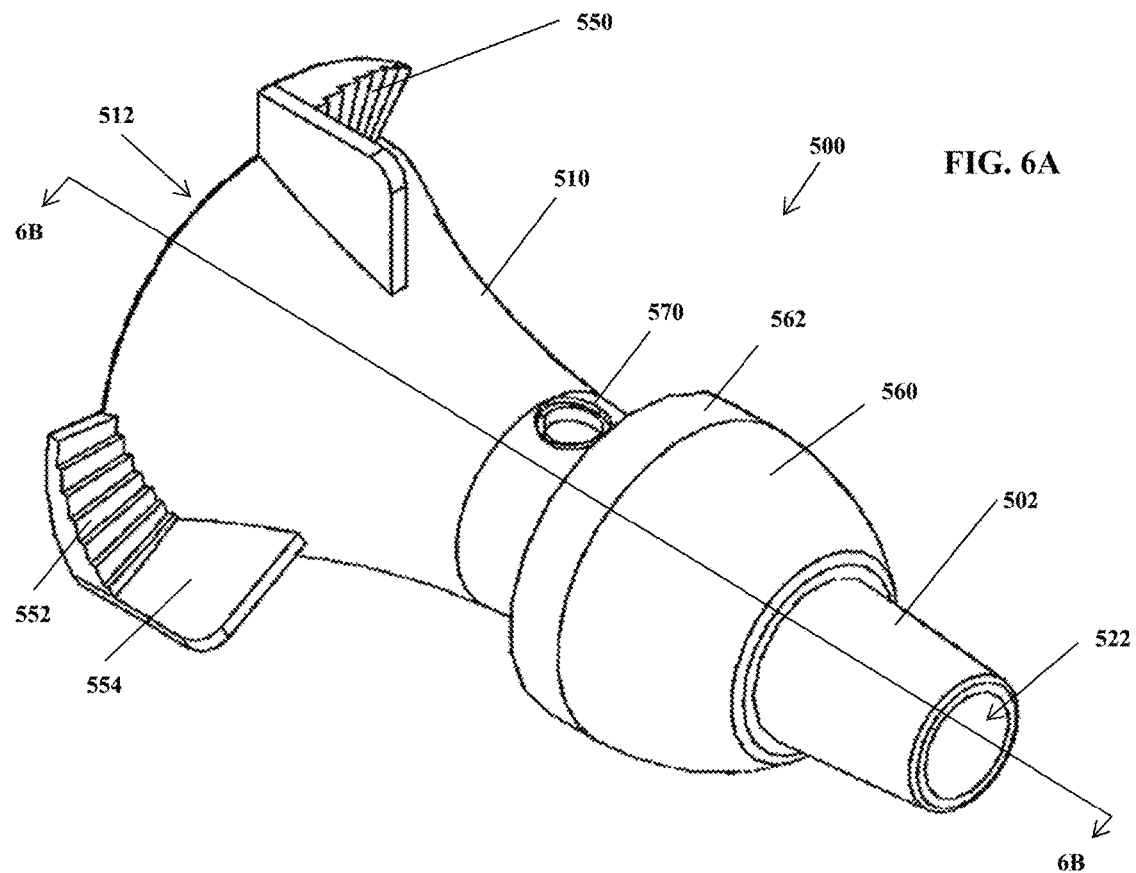
FIG. 6A is a perspective view of one embodiment of the speculum tip.
Figure 6B:
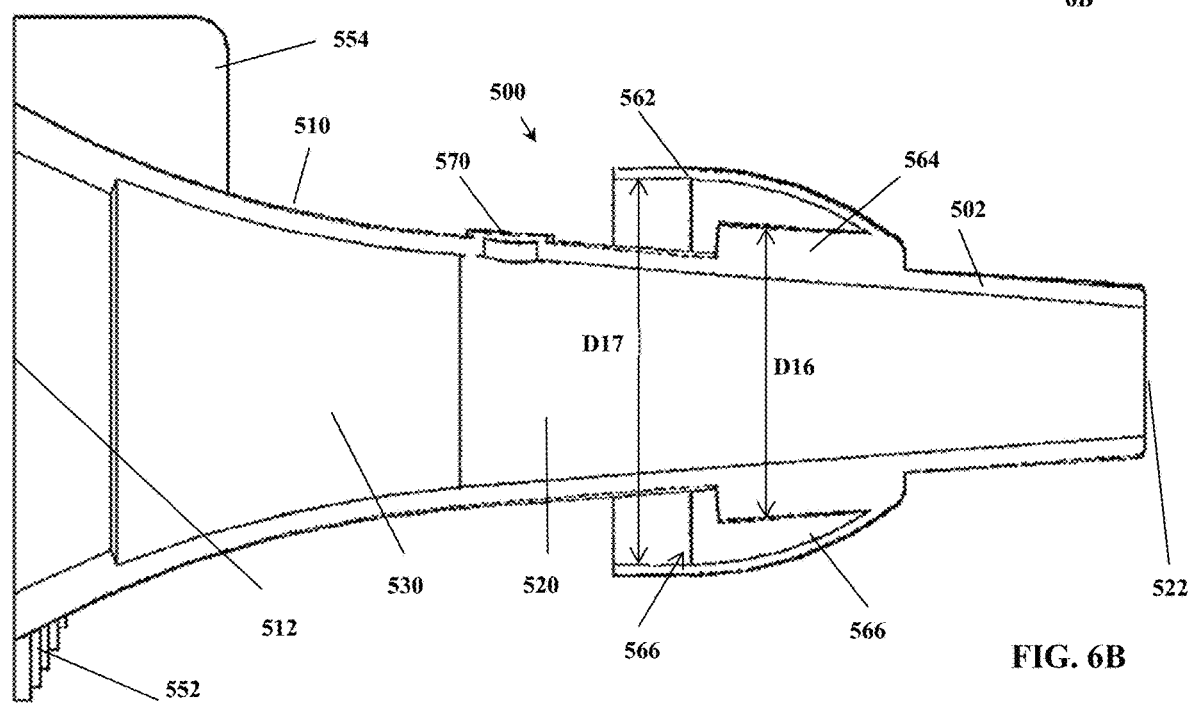
FIG. 6B is a cross-sectional view of one embodiment of the speculum tip taken along line 6B-6B from FIG. 6A.

Another embodiment of the speculum tip 500 is shown in FIGS. 6A-6B. Similar features and elements are present in the speculum tip 500 as in the speculum tips 100-400 with an additional sealing feature 560. Any of the previous speculum tips 100-400 may include a sealing feature 560 if the toroidal vortex is unable to be generated for any reason, or has superior structural integrity when a sealing feature is incorporated. Difficulties in generating the toroidal vortex may range from canal anatomy, earwax protrusions, or pneumatic malfunctions in the otoscope. The sealing feature 560 is coaxially disposed around the exterior surface of the distal tip region 502. The sealing feature 560 made of such material as silica gel or memory foam, and is integrated into the speculum tip 500 to ensure a quick and easy seal of the ear canal of the patient. Alternative materials include (b) polymers, such as polyvinylchloride, nylon, polytetrafluoroethylene, polystyrene, acrylonitrile-butadiene styrene, polypropylene, and other suitable plastics; or (c) ceramics, such as silicon carbide, tungsten carbide, apatite, and other suitable ceramics; wherein the suitable metals, alloys, plastics, or ceramics respectively have a tensile strength sufficient to maintain a tubular structure and are capable of being sterilized for medical use. The sealing feature 560 may be designed in different sizes: a smaller diameter model with less distance between the sealing feature 560 and distal end of the tip for infants and young children, as well as a standard, larger model, with more distance between the sealing feature 560 and distal end of the tip, to accommodate deeper ear canals found in older ears. The sealing feature 560 includes a lip region 562 coaxially extending around a distal shaft region 564, which creates a lipped lumen 566 between the distal shaft region 564 and the exterior surface of the distal tip region 502. The lip region 566 axially moves towards the exterior surface of the distal tip region 502 when the speculum tip 500 is disposed within an ear canal. The lipped region 562 is biased to extend axially away from the exterior surface of the distal tip region 502 as to create a seal against the ear canal. The lipped region 562 may include elastic or superelastic materials that provide resistance to mechanical deformation. The lip region 562 includes a diameter D17 and the distal shaft region 564 includes a diameter D16. The diameter D17 is greater than the diameter D16 as to create the lipped lumen 566 between the distal shaft region 564. The distal shaft region 564 is secured to the exterior surface of the distal tip region.

As shown in FIGS. 6A-6B, the speculum tip 500 includes a thin membrane 570 traversing the thickness of the distal tip region 502. The thin membrane 570 functions as a pneumatic fuse in and designed to give way before enough pressure would be delivered to damage the eardrum. A user may potentially damage the eardrum with an absolute seal of the canal, when compared to the poor seals currently available. The thin membrane may include a diameter of about 2 mm, which will burst or unseal when the pressure builds up in the ear canal about a particular threshold limit.

The speculum tip 500 includes a generally conical configuration with a narrow distal tip region 502 longitudinally extending from a larger proximal region 510. The distal end of the central shaft lumen 520 includes a distal opening 522 through which a delivered puff of fluid displaces the eardrum. The proximal region 510 includes a proximal opening 512 operably coupled with a proximal lumen 530 disposed within the proximal region 510. The proximal lumen 530 includes a conical cross-section or profile that narrows to the central shaft lumen 520. The speculum tip 500 includes a plurality of flanges 550 surrounding the proximal end of the proximal region 510. The flanges 550 include a stepped portion 552 descending from the vertical lip 554. The flanges 550 are used to secure the speculum tip to an otoscope as to provide the user a grip-like structure to twist or rotate the speculum tip 100 about its longitudinal axis. The flanges 150 may be removed from the speculum tip 100 depending on the otoscope features for securement.

Figure 7A:
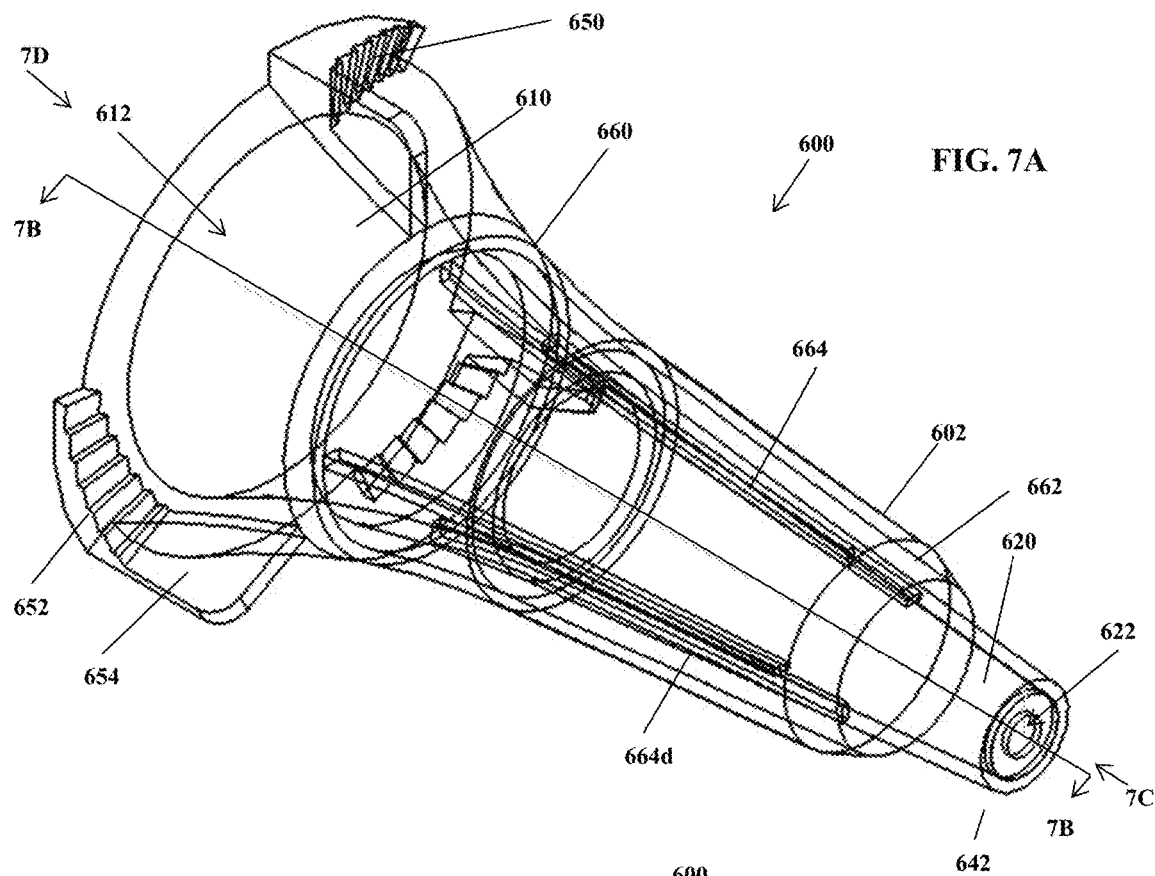
FIG. 7A is a perspective view of one embodiment of the speculum tip.
Figure 7B:
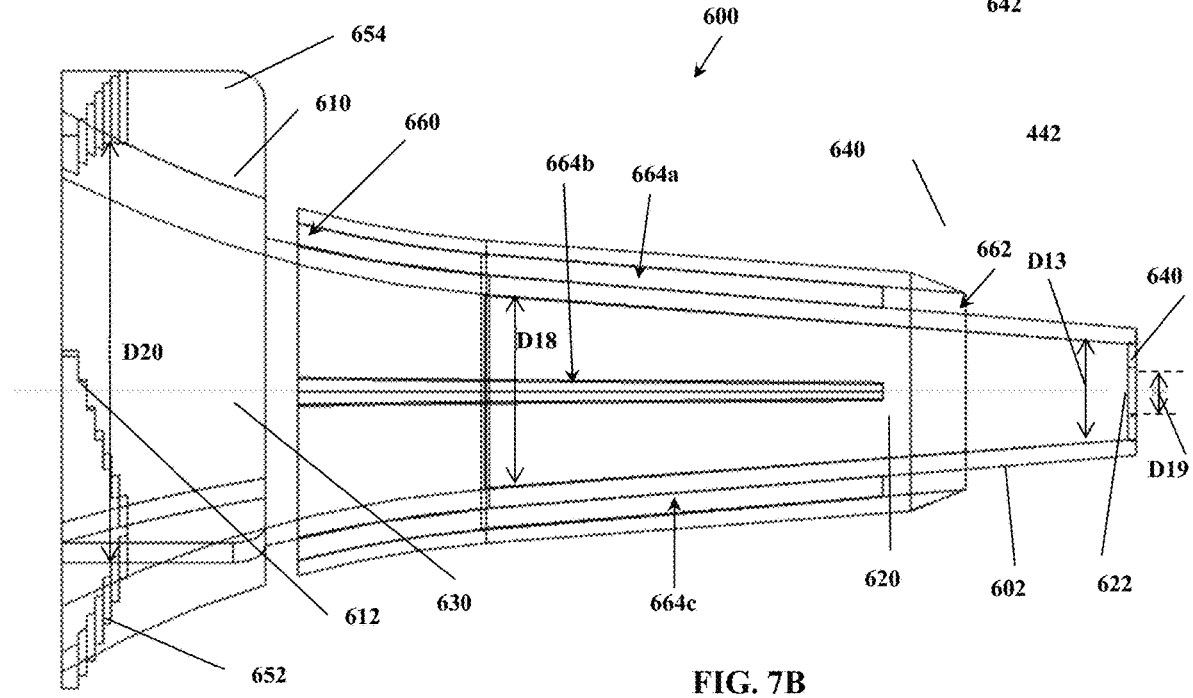
FIG. 7B is a cross-sectional view of one embodiment of the speculum tip taken along line 7B-7B from FIG. 7A.

Another embodiment of the speculum tip 600 is shown in FIGS. 7A-7B. Similar features and elements are present in the speculum tip 600 as in the speculum tips 100-400 with a proximal air escape outlet 660 and a distal air escape inlet 662 fluidly coupled with an air passageway therebetween 664. Any of the previous speculum tips 100-400 may include the proximal air escape outlet 660 and the distal air escape inlet 662. The speculum tip 600 includes a generally conical configuration with a narrow distal tip region 602 longitudinally extending from a larger proximal region 610. The distal tip region 602 includes a coaxially disposed central shaft lumen 620. The proximal region 610 includes a proximal lumen 630. The air passageway 664 is separate from the central shaft lumen 620 coaxially surrounds the central shaft lumen 620 by a plurality of air passageways 664a, 664b, 664c, and 664d. The air passageway 664 terminates around the proximal lumen 630 by the air escape outlet 660 and extends from a portion of the distal region 602. The air passageway 664, the proximal air escape outlet 660 and the distal air escape inlet 662 ensures that air delivered through the central shaft lumen 620 will not be sent into a sealed ear canal. A sealed canal could be potentially dangerous to the patient due to rapid expansion of volume in the sealed canal. The speculum tip 600 forms no seal with the ear canal due to the air passageway 664, the proximal air escape outlet 660, and the distal air escape inlet 662 and generates a toroidal vortex by fluid traversing through the outer lumen 620, as shown in FIG. 7A-7B. The distal end of the central shaft lumen 620 includes a distal opening 622 and a distal lumen lip 640 coaxially disposed within the distal tip region 602. The distal end of the central shaft lumen 320 includes a distal lip 340 that surrounds a distal opening 622 as to create a smaller distal opening 622 compared to the distal end of the central shaft lumen 620. The central shaft lumen 620 and the proximal lumen 630 include a conical cross-section or profile that narrows to the distal opening 622.

The proximal region 610 includes a proximal opening 612 operably coupled with the proximal lumen 630 coaxially disposed within the proximal region 610. The proximal lumen 630 includes a conical cross-section or profile that narrows to the central shaft lumen 620. The speculum tip 600 includes a plurality of flanges 650 surrounding the proximal end of the proximal region 610. The flanges 650 include a stepped portion 652 descending from the vertical lip 654. The flanges 650 are used to secure the speculum tip to an otoscope as to provide the user a grip-like structure to twist or rotate the speculum tip 600 about its longitudinal axis. The flanges 650 may be removed from the speculum tip 600 depending on the otoscope features for securement.

In one embodiment, the walls of the central shaft lumen 620 are separated by about 0.1 to about 15 mm as to create the double-curling air vortex ring exiting the distal outer opening 622. The central shaft lumen 620 includes a diameter D18 that is narrowed by the distal end of the central shaft lumen 620, as shown in FIGS. 7A-7B. The distal outer opening 622 includes a diameter D19 that creates a smaller circular opening than the diameter D18 of the distal end of the central shaft lumen 620, as to produce an air vortex ring. As such, the diameter D19 is smaller than the diameter D18.

The proximal lumen 630 includes a distal end with a diameter D20 that coaxially aligns with the proximal end of the central shaft lumen 620, as shown in FIG. 7B. The diameter D20 is larger or greater than the diameter D18 of the central shaft lumen 620, such that the central shaft lumen 620 includes a generally trapezoidal cross-section or profile. The second outer lumen 440 includes a proximal outer opening 442 with a diameter of D14. D20 includes a diameter to allow for sufficient field-of-view for imaging and also D20 includes a diameter that is structurally sound to interface and administer the pneumatic pulse without structural issues/failure. The toroidal vortex is generated by fluid passing through the inlet 652, traversing the central shaft lumen 620, and exiting the distal outer opening 622. The drag forces from the inner and outer diameter surfaces along the central shaft lumen 620 cause the behavior of the toroidal vortex.

EXAMPLES

The following examples are put forth so as to provide those of ordinary skill in the art with a complete disclosure and description of how the systems, articles, devices, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1: the Airflow Requirement to Achieve Noticeable Displacement of the Eardrum in the Speculum Tips Speculum tips 100-500 are tested to determine the requirements and limitations of use of the designs. Each prototype will be used to deliver bursts of air to a synthetic eardrum located ~5 mm away from the speculum tip, similar to the clinical use case. Multiple dynamic stimuli, including a traditional pneumatic insufflation bulb and various sizes of plunger syringes will be used to deliver a known volume of air between 0.25-5 cc delivered at pressure between about 10 mmHg and 100 mmHg over a known duration to determine the flow required to achieve visible displacement of the synthetic membrane. The known duration may be between about 50 ms to about 1000 ms. Each Speculum tip 100-500 will be compared to evaluate performance, with total membrane displacement as a key metric. Once these data are taken, analysis to determine the suitability of using a traditional pneumatic insufflation bulb with the Speculum tips 100-500 will be performed. It will be important to determine whether separate stimulus will be needed to produce the required displacement or whether our product can be used with existing pneumatic insufflation bulbs.

Figure 8:
FIG. 8 is a photograph of the Life/form pneumatic otoscopy kit, which will enable experimental testing of speculum tips.
Figure 10A:
FIG. 10A is a photograph of pediatric and adult standard disposable tips.
Figure 10B:
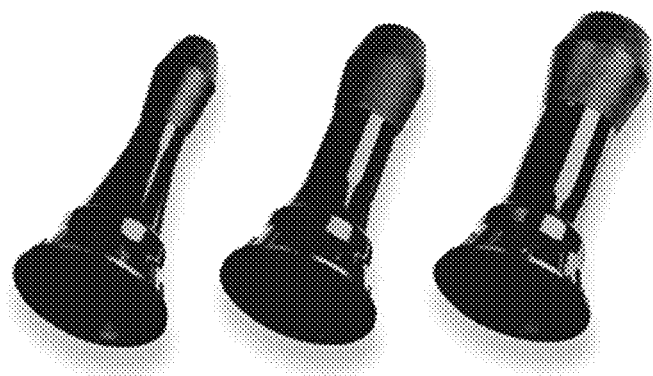
FIG. 10B is a photograph of Welch Allyn's recently introduced SofSpec tip.

Example 2: the Displacement Induced by the Speculum Tips 100-500 Compared to that Induced by Traditional Pneumatic Methods Using a Standard or SofSeal Speculum The purpose of the pneumatic exam is to displace the eardrum and qualitatively assess the amount of motion to determine the pressure in the middle ear. It is therefore important to quantitatively compare each Speculum tip's 100-500 ability to displace a synthetic membrane and compare each to current commercial solutions. For this experiment, the Life/form ear model, as shown in FIG. 8, will be utilized and each of the Speculum tips 100-500, as well as a standard otoscope speculum (FIG. 10A) and Welch Allyn's SofSpec product (FIG. 10B) will be used to displace the membrane. The Life/form ear model instructions can be found at http://www.globalnasco.com/pdfs/Health_Care/manuals/LF01090.pdf, herein incorporated by reference in its entirety. The Speculum tips 100-500 will not rely on a seal of the ear canal; while the standard and SofSeal specula (FIG. 10B) will be operated as they are meant to, requiring a seal of the ear canal. The membrane displacement will be measured using an OCT imaging system, as described in U.S. Pat. Nos. 8,115,934 and 8,594,757, herein incorporated by reference in their entireties. This imaging system is capable of detecting deflections on the order of ~5 microns and will be responsible for measuring the amount of displacement from each speculum tip. This will allow a true quantitative comparison of each tip. The imaging will be done from the middle ear side of the synthetic membrane, while the air stimulus will come from the ear canal side of the membrane.

Example 3: Sealing Feature Providing a Better Seal of the Ear Canal

A direct and quantitative comparison of silica gel and memory foam may determine which will be best for sealing the ear canal. Crafting an experiment to use each speculum tip on an anatomically correct pediatric ear model will assess which material is better suited to this application. An anatomic model called the Life/form pneumatic otoscopy kit (FIG. 8) will be used to evaluate the technologies proposed in this application.

Figure 9:
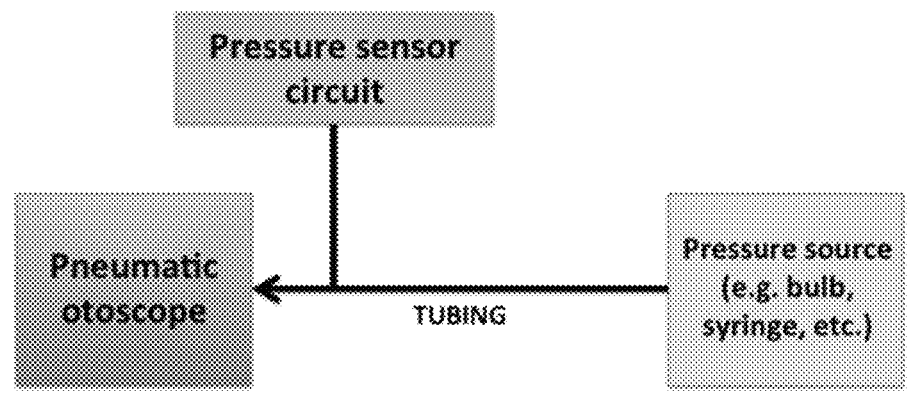
FIG. 9 is a schematic of the proposed system design for monitoring ear canal pressure in real time.

For this experiment, an insufflation bulb using standard pneumatic techniques will modulate the ear canal pressure in the Life/form model as shown in FIG. 8. A calibrated pressure sensor will be connected to the system in a 'T' configuration, as shown in FIG. 9, to monitor the canal pressure in real time. After ensuring the system has no leaks aside from potential leaks due to poor sealing of the canal, the seal quality will be quantified by measuring how quickly the pressurized canal loses pressure. This will allow quantitative comparison of the proposed models with each other, as well as existing solutions.

Example 4: how Much Improvement is Obtained by Using the Sealing Feature 560 Over Standard and SofSeal Specula?

Using the experimental setup previously described in FIG. 9, a quantitative comparison of the Sealing Feature 560 will be made with traditional commercial otoscope tips and the Welch Allyn SofSeal pneumatic tips. Angle of insertion will be varied in this comparison, and time to obtain a seal will be measured, as this is a critical parameter to the time-constrained physician.

Example 5: Generate Vortip Specula Designs in SolidWorks and Empirically Test and Characterize the Produced Vortices for Each Model Using a Pneumatic Bulb Stimulus Weveral models, using CAD software (SolidWorks), were generated that utilize thermodynamic principles. These designs were then 3-D printed using a standard PolyJet printer and tested empirically using the same experimental setup as indicated above, but smaller scale, as shown in FIG. 11A.

FIG. 11A is a photo of the specula testing chamber for video capture of expelled air puff behavior from both commercial and the speculum tip 100, 200, and 300; FIG. 11B is a photo of FIG. 11A with the brightness and contrast enhanced to better visualize the vortex ring (green arrow) produced by the speculum tips 100, 200, and 300; FIG. 11C is a side view of the speculum tip embodiments tested showing the standard commercial design, a straight cylinder design 100, an expanding or negative taper design 200, and a flange design 300. Each speculum tip tested was sealed on the backside using plastic sheeting and superglue, then connected to the pneumatic bulb through a hole in the center of the plastic sheeting. This assembly was then mounted into a custom wooden frame and the speculum tip was filled with liquid smoke. Testing proceeded with video capture of the behavior of possible vortex rings produced by pneumatic bulb presses over a ~5 second interval. The videos collected were then used to 1) confirm vortex ring possibility and 2) measure the average velocity for each trial by measuring the leading edge of the smoke rings (or puff, if no ring) over the duration of the recorded video frames.

The commercial specula did not generate vortices, while the speculum tips 100, 200, and 300 were able to intermittently produce vortex rings using the standard pneumatic bulb stimulus delivery method. Of all the Vortip designs though, the design with a flange 300 at the distal tip was best at reliably producing stable vortex rings compared to the other 2 Vortip designs 100 and 200. To reduce this variability, likely caused by user input (i.e. grip strength and speed of use of the pneumatic bulb), an automated stimulus generator was developed in the following Objective.

FIGS. 12A-12D are graphs showing the air velocities of the speculum tips in FIG. 11C including the current commercial specula design, the three Vortip designs produced similar air velocities with smaller standard deviation and range. The flange Vortip embodiment 300 produced the most stable and consistent vortex rings compared to the other two Vortip embodiments 100 and 200, which was observed both qualitatively and quantitatively.

Discussion

The purpose of this example was to investigate the ability of our novel specula designs to generate a vortex ring, which, by its nature, will conserve momentum (and thus impulse) much better than a standard air jet. This involved conceptualizing and prototyping novel speculum designs based on information gleaned from optimizing vortex generation in cardboard box models. Through this empirical approach, the best results from flange-style designs were found with an outer-to-inner diameter ratio of about 4/3. Each of the designs evaluated has pros and cons. The largest tradeoff that must be made when choosing to go with the flange design is accepting a smaller aperture at the distal end of the speculum. This aperture defines the maximum field of view obtainable using the otoscope. While physicians always desire the largest field of view possible when assessing an eardrum, they also told us that a modest reduction will not affect their ability to find or assess the eardrum. The necessary reduction in field of view will enable a significant increase in diagnostic ability by enabling an easy and reliable pneumatic exam.

This objective culminated in an experiment comparing performance of the commercial tip alongside the three Vortip designs using a manual bulb squeeze. Velocity was chosen as the performance metric, although quality of the vortex ring was also considered qualitatively through observation. While all models tested had similar velocities (in fact, the flange design was a bit lower than the others), the flange design was the most consistent. The flange design also produced the highest quality vortex rings based on visual inspection. For these reasons, the flange Vortip design was moved forward for further testing. It is worth noting that all Vortip specula produced visible vortex rings, where the commercial standard speculum tip did not. Furthermore, the velocities measured in the standard commercial tip trials were measured as the leading edge of the air jet since no vortex could be measured. Since the velocities measured were average velocities, it should be noted that the standard commercial tip decelerated significantly more than the Vortip designs, but likely had higher jet velocity near the tip exit.

Example 6: Characterize the Impulse Resulting from a Bolus of Air Through a Standard Otoscope Speculum (Jet) and the Vortip Specula Designs (Vortex Ring) Using an Automated Stimulus Generator Task 1: Build and Characterize an Automated Stimulus Generator.

To start, several different design options were explored for developing a prototype of the automated stimulus generator. These proof-of-concept device designs included (1) a solenoid-operated piston and cylinder module, (2) a spring piston and cylinder module, and (3) a compressed air module. The (1) solenoid-operated piston module could be electrically controllable but would be more expensive than the other modules considered, and has size (fairly large) and power (>120V power supply needed) shortcomings. The (2) spring piston and cylinder module would have similar drawbacks and, while less expensive than the solenoid-operated option, this option could suffer from less precise repeatability and possible mechanical failure inherent to any device with moving parts. The (3) compressed air module would utilize a pressurized cylinder, which are compact, inexpensive, and can produce multiple repeatable pulses per unit. These pressurized cylinders are easy to attach/detach to a solenoid valve and pressure output can be easily adjusted via a regulator. Additionally, an air compressor was considered, however these are loud, expensive, and lack any benefits over a pressurized cylinder other than no need to replace cartridges.

Therefore, the final design, shown in FIG. 13B, consists of a pressurized cylinder connected to a solenoid valve via a regulator. The solenoid valve was designed to be electronically controllable using a custom-designed circuit. Electrical pulses of programmable duration and width can be produced by the circuit such that a trigger button (user input) could be used to open/close the valve for a pre-specified amount of time, not dependent on the duration of the user button press, to initiate and release a controlled and consistent stimulus pulse of air.

Here, each of the subcomponents of the automated stimulus generator shown in FIG. 13A is described.

Pulse module and button: The purpose of the pulse module block is to provide a more reliable and repeatable signal to control the opening and closing of the solenoid valve. Manually controlling the operation of the valve with a button alone would lead to considerable variations in pulse length (and thus valve opening time) between trials. Such user-dependent variations would not allow for repeatability and control over the delivered air puff beyond that currently accomplished with the pneumatic bulb, and are therefore impermissible, as control and reduction of user input variability is paramount. Additionally, precise control and repeatability are necessary for accurate assessment and comparison of the performances of different speculum designs or different supply pressures.

Pressurized $CO_2$ supply: The purpose of the pressurized $CO_2$ supply/canister is to provide an inexpensive, portable, and reliable source of pressurized air for generating the air puff stimulus and consequent eardrum modulation.

Pressure Regulator: The purpose of the pressure regulator, with build-in gauge, between the compressed air source (cylinder/canister) and the solenoid valve is the necessity to step down the canister pressure (typically ~850-900 psi) to the desired output pressure (~1 psi) necessary for safely modulating the eardrum.

Solenoid Valve: The purpose of the solenoid valve between the pressure regulator and the output tubing is to produce a pulse release of compressed air sufficient for modulating the eardrum. The solenoid valve is electrically controlled by the pulse module circuit and button.

Troubleshooting: During the construction and performance testing of the automated stimulus generator, several reasonable development issues arose. After assembly of the customized circuit was completed, during performance testing sometimes a single button press would generate two or more resulting pulses in a row. This was ultimately narrowed down to bounce noise in the LTC 6993, which was replaced with a more precise model (LTC 6994) that included a debouncer.

The LTC 6993 looks for a rising-edge above a certain voltage threshold on the IN signal to trigger the output pulse. If a rising-edge of sufficient voltage was found, the LTC 6993 would trigger. The LTC 6993 would not retrigger or be affected by additional rising edges on the IN signal until the output pulse was completed, after which a subsequent pulse could be triggered. To test that this module has a consistent and adjustable pulse width in the design range, five values for Rset were chosen to cover the design range of the automated stimulus. An oscilloscope captured the trace of the resulting pulse and the pulse width was measured and compared well to the value predicted by Rset.

To test that the addition of the LTC 6994 (with a programmed 250 ms delay time) eliminated the multiple pulse problem, which sometimes resulted from rapid button pressing or pressing and holding the button, similar test for "consistent and adjustable pulse width generation" was conducted. The same five values for Rset as the previous test were used and two scenarios were tested for each: (1) rapid and successive button presses do not generate pulses of the incorrect width (such as overlapping pulses or an output that is not a pulse at all, such as getting "stuck" on higher voltage resulting in an open valve) and (2) pressing and holding the button does not result in more than one pulse, specifically, a second pulse trigger when the button is released.

FIG. 14 shows representative oscilloscope traces of these tests. Each pulse duration was repeated 20 times, and no deviation in pulse duration was observed down to 1-microsecond precision. The standard deviation of the pulse duration ranged from 3 microseconds up to 18 microseconds, and was smaller with smaller pulse durations. This test proved that the circuitry designed and built for pulse generation worked as intended and was sufficiently repeatable for our purposes.

Discussion

This CO2 cartridge design is cheaper, less bulky, and likely more precise than a piston chamber would be. Furthermore, a piston chamber could result in a significant amount of "kick" that would cause motion in the otoscope, complicating analysis of its results and potentially creating a safety concern. The small amount of air released from the cartridge would cause minimal bulk motion of the otoscope, and the cartridge design can be made compact enough to fit into a traditional otoscope form factor.

As shown in the data, the circuitry controlling the regulator is very precise. This is important to ensure repeatable stimuli. If a large amount of interpulse variation exists then quantitative analysis becomes much more difficult.

Short pulses are important for vortex generation, in order to allow entrainment of surrounding air into an efficient vortex ring.

This Objective culminated in an experiment directly comparing average velocity generated from the flange Vortip design with (1) a manual bulb squeeze stimulus, and (2) a stimulus from the automated pulse generator. The automated stimulus drastically improved the standard deviation of the velocity, as expected. In the current measurement configuration, distance can only be measured to 1 mm of precision, and at that level of precision there was no measured variation between trials. The experiment may be modified to allow more precise measurements. Note, also, that this low variance was at much higher velocities than those in the manual case. Clearly, the automated stimulus is an important addition that will help reduce user variability. Furthermore, it should be noted that the quality of the vortex rings created by the automated stimulus were far superior to those of the manual bulb squeeze, traveling further and holding their shape better. This is likely due to the ability to precisely control the pulse duration and use shorter pulses than those able to be produced manually.

Example 7: Measure Mechanical Impulse from Standard and Vortip Specula Using an Automated Stimulus Generator The testing conducted in Example 5, Example 7 was repeated after switching out the traditional commercial pneumatic bulb for the automated stimulus module. Due to the success of the flanged Vortip design in all prior tests, this design's performance with the automated stimulus module is highlighted in FIG. 15. Using the input parameters of the prior Example 6, data was collected until at least 12 trial datasets were collected without possible system complications, such as occurrence of double pulses. As shown in FIG. 15, by switching out the pneumatic bulb for the automated stimulus module, more reliably consistent vortex rings were produced from the Vortip specula, albeit standard deviation and range values sub-resolution due to limitations of the detection method used. By more precisely controlling the produced vortex ring velocity, the impulse delivered to the eardrum can be consistent both intra- and inter-user, which is a great improvement upon the variable results from the pneumatic bulb and consequent usefulness of exam results toward a diagnosis. The increased velocity for the automated stimulus (6B) is likely a result of (1) the much shorter pulse durations (30-100 ms instead of 250+, like during manual), leading to more efficient vortices, and (2) faster initial jet velocity produced from the highly pressurized air supply.

Example 8: Measure Deflection of a Life/Form Ear Model Membrane after Stimulus with Standard Specula and Vortip Specula Using a Custom Video Analysis Algorithm The human eardrum is a highly complex tissue whose biomechanical composition is of great interest to physicians with regards to management of various diseases (13). This tissue is therefore difficult to replicate in the lab for mechanical testing, however, a sufficiently replicative eardrum phantom model was developed. Several possible eardrum tissue models were evaluated, from man-made commercial plastics (i.e. Ziplock bags) to natural biomaterials (i.e. porcine small intestinal submucosa). The porcine small intestinal submucosa (SIS) provided the most anatomically replicative response when incorporated into our Life/form ear model and tested under standard video pneumatic otoscopy. This is not particularly surprising, as temporalis fascia and cartilage are commonly used as grafts for the eardrum in tympanoplasty procedures, and all three of these materials contain a large amount of collagen and elastin, similar to a human eardrum. In fact, SIS has been tested as a scaffolding material for TM grafts as well, and performed as well as the fascia and cartilage grafts.

The Life/form ear model was chosen to represent the ear canal and middle ear space. As shown in FIG. 16A, this model consists of a pediatric sized head with removable ears. The ears contain an anatomically accurate canal, and modular inserts for the eardrum and middle ear cavity. The eardrum can be replaced and is held on with an o-ring.

The middle ear can be pressure-controlled and fluid can be placed directly in the cavity to simulate disease states. Replacing the standard synthetic plastic membranes that come with the Life/form model with the SIS membranes described above produced a sufficient model.

Development

Testing throughout this objective was conducted using (1) the full Life/form ear model, (2) a cutaway version (removing the external ear for ease of experimental setup) of the Life/form ear model, and (3) a tympanic membrane model that consisted of the TM mount and grommet within the Life/form ear model (i.e. just a membrane with no canal at all). These configurations can be seen in FIG. 16B. A wooden mount was crafted to further enhance the stability of the models during experimentation.

Material verification: Air puffs were statically loaded onto the TM using a standard pneumatic otoscopy insufflation technique. Video otoscopy was used to analyze the deformation of the plastic films (1.5 mils Ziploc sandwich bags and 3 mil heavy duty freezer bags) and the SIS. These results were then compared to the deflection seen from the human TM during standard pneumatic otoscopy to determine which material deflects most similar to a human TM. Far and away, the SIS material most closely resembled the deflections seen in a typical human membrane in a clinical setting, validating our choice in material. For length reasons, this data is not shown here, but can be found in the supplemental data folder linked at the end of the report.

Development of an algorithm for video analysis: As part of an effort to simplify the pneumatic otoscopy exam and remove subjectivity, some preliminary work was done in developing algorithms capable of automatically estimating deflection of the eardrum purely from the video, utilizing the intensity information in each frame image. It is noted that the video otoscope used (Welch Allyn Macroview) has the features of auto-exposure and auto-gain for better viewing the TM. Since these algorithms are to perform well regardless of otoscope model or settings, these features were not disabled during the experiments. However, for a correct representation of the TM deflection based on image intensity, the effects of auto-exposure and auto-gain have to be compensated. In order to do this, the TM area for each video was delineated and the rest of the frame was considered as the "background." For each frame image within one video, the intensity was scaled based on the sum of all the background pixel values, and then the mean intensity of TM area was calculated as the value representing TM deflection. FIG. 17 illustrates one example with two different TM deflections. FIGS. 17A and 17B were two images from the same video. The area within the yellow dashed circle on each image is used as TM area. After auto exposure and auto gain compensation, the mean intensity value within the yellow dashed circle was 131.4 and 72.15 for FIGS. 17A and 17B respectively, clearly indicating different TM deflections. After all the values from all the frame images within one video were calculated, the results were then vertically shifted such that 0 corresponds to the TM deflection at rest state.

The goal of this algorithm development was to investigate a low-overhead method for estimating TM motion. This intensity-based algorithm is simple to implement in real-time and can be executed on nearly any modern computing device, making it very flexible. However, the main limitation is insensitivity to deflection directionality. Since intensity changes are measured, rather than tracking features, some deflections may look similar regardless of whether the membrane deflects laterally or medially, leading to some ambiguity in direction. Generally, physicians are simply looking for an estimation of magnitude of movement to determine whether the membrane is mobile or not. For this purpose, the algorithm described, as well as automated stimulus module, work well. Considered together, as shown in FIG. 18, one possible use case would be if a physician could start with a low pressure air puff, then increase slowly by adjusting the automated stimulus module resistance until TM deflection can be detected. As proof of concept, in FIG. 18, TM deflection behavior is shown for three different pulse durations on the automated stimulus generator. Note that the difference between deflection from 33 ms to 66 ms seems proportional, but the difference from 66 ms to 100 ms is not. This could be due to saturation effects of the membrane. As it is pushed further from its rest state, the restoring force becomes greater, which would result in a non-linear response as pressure increases.

Future efforts will investigate more complex algorithms based on feature recognition and tracking that may provide robust directionality in addition to magnitude of motion. Another limitation is related to hardware. The Welch Allyn Macroview video scope used for these experiments is limited to 30 frames/s, which means the temporal sampling is only 33 ms, which is quite sparse when examining response to pulses in the 30-100 ms range. This leads to undersampling, which leads to artificial variations in peak magnitude. In future work, this limitation will be overcome by moving to a higher frame rate camera, as these are readily available at low cost due to recent innovation in the mobile phone market.

Example 9: Validate Custom Video Analysis Algorithm Using Simultaneous Optical Coherence Tomography During Detection of Eardrum Model Deflection This Example represents combining the Vortips designed in Example 4 with the automated pulse module designed in Example 5. An array of variables are tested (FIG. 19) to investigate the comparative performance of the Vortip prototype in a variety of anatomical situations and varied stimuli. Additionally, in-house optical coherence tomography (OCT) systems were used as a gold standard measurement for deflection in these experiments, as they are well understood and accepted in the metrology and clinical communities. OCT is a type of optical imaging analogous to ultrasound except OCT uses near-infrared light instead of sound. This allows these systems to be able to resolve motion down to 5-10 microns in real-time, and, specifically, precisely detect TM motion during pneumatic otoscopy.

Figure 19:
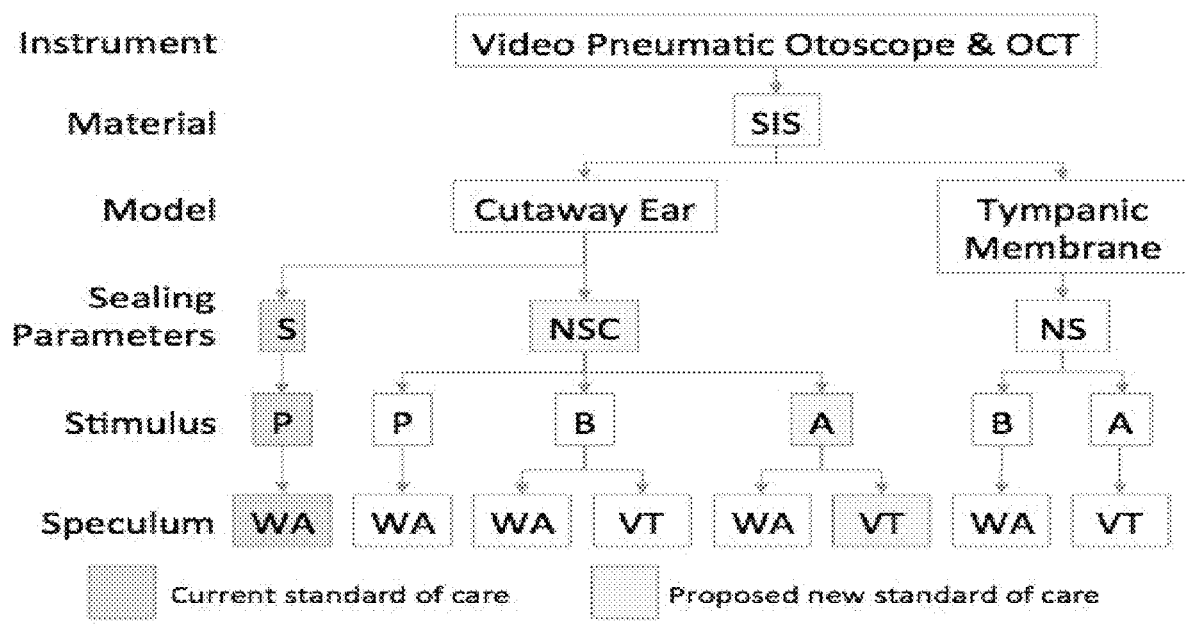
FIG. 19 is a schematic diagram showing the test matrix showing all varying parameters tested in this objective. This covers variables such as sealed vs. unsealed, manual (pneumatic bulb) vs. automatic stimuli, and current commercial (Welch Allyn) specula vs. our novel Vortip specula. The gray shaded arm shows the current clinical standard and the light blue shaded arm shows the new standard proposed from this work.

Vortip performance evaluation: In this experiment, a matrix of membrane deflection data is generated under varying conditions (FIG. 19). Each variable parameter is shown on the left and each case tested is shown in the matrix. The gray (far left) shaded arm represents the current standard of care (standard pneumatic otoscopy under a perfectly sealed condition), and the light blue shaded arm (right) represents the proposed new standard of care using our technique (automatic, seal-less pneumatic otoscopy with Vortip specula).

Figure 20:
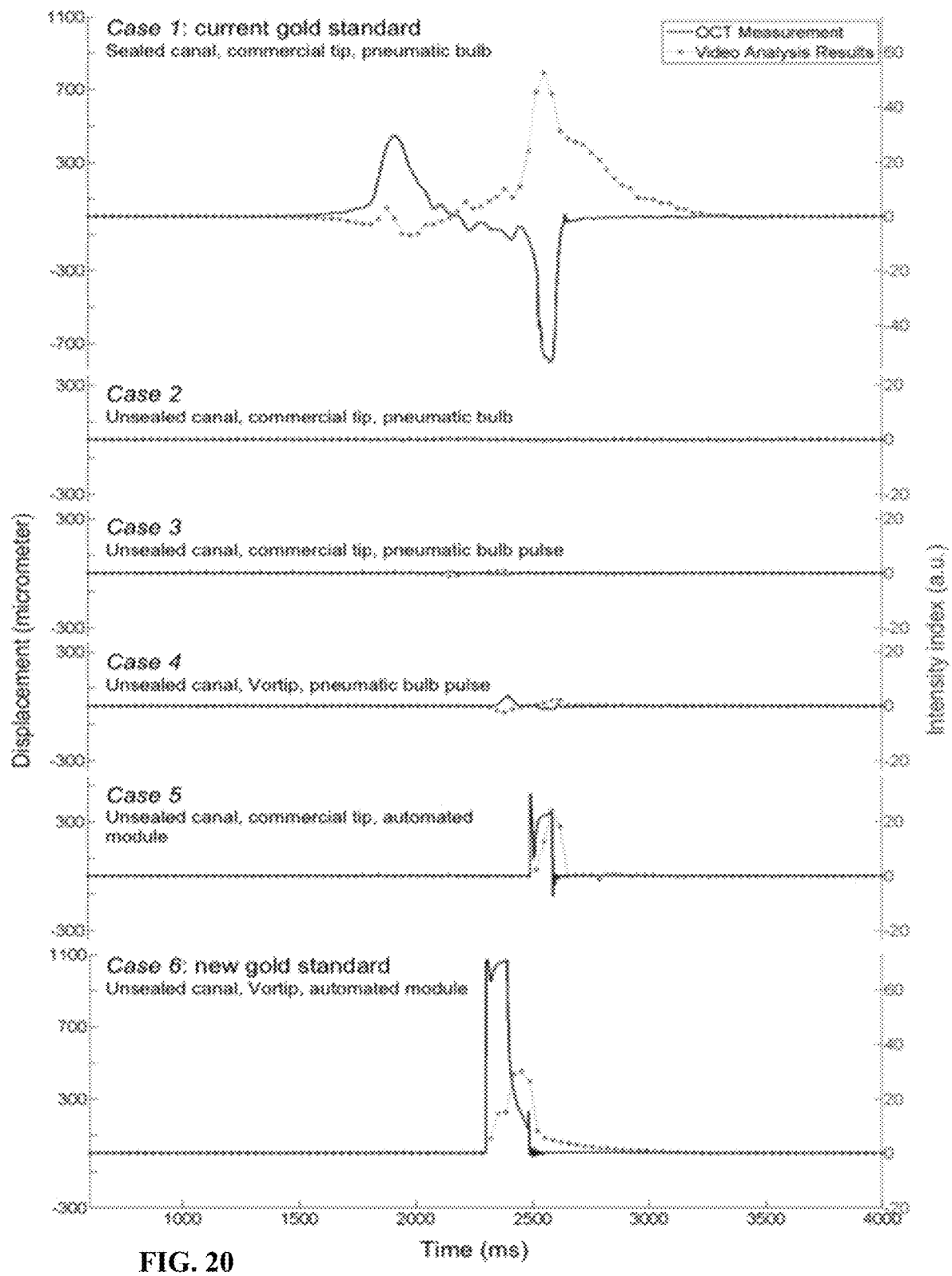
FIG. 20 is a graph showing the comparison of 6 key cases comparing the use of standard commercial vs. Vortip specula and standard pneumatic bulb vs. automated stimulus module. Deflection of the eardrum model was detected via optical coherence tomography (blue, solid line) and custom video algorithm (red, dotted line).

The story of this Objective is summarized in FIG. 20. Case 1 represents the current gold standard of pneumatic otoscopy under a sealed canal. This situation rarely happens because getting a seal is difficult. Often, what a user ends up with is Case 2, where standard pneumatic otoscopy is used, but without a seal, the exam is rendered useless (and leaving the user assuming the membrane is not moving). Case 3 shows that even if the user squeezes the bulb quickly, no deflection is produced in the commercial specula. However, the same scenario in Case 4, but with our novel Vortip design generates a deflection measurable using both OCT and our deflection estimation algorithm. Finally, Cases 5 and 6 compare the commercial and Vortip specula, respectively, in an unsealed condition with the automated stimulus developed in Objective 2. Both generate detectable deflection; however, the Vortip generates nearly twice the deflection of the commercial tip. This behavior was repeatable and consistent, and strongly validates our approach and design.

Discussion

While an automated algorithm for deflection based on the video otoscopy feed was not conceived as part of the original proposal, it was an important addition to prove the concept that automated analysis of motion could be done in real time. The intensity subtraction method chosen was quite basic, but very low overhead and a good first effort. The algorithm accurately represents motion in most cases, although it occasionally gets confused if there are concentrations of increasing and decreasing pixels simultaneously in the same image due to a particular angle or geometry. In future work, feature-based algorithms will be investigated, which will have higher specificity and directionality. A robust algorithm to estimate motion of the eardrum will be important to minimize the experience curve in the interpretation of pneumatic otoscopy. Currently, experience plays a large part in the ability of a user to accurately interpret pneumatic otoscopy. Interpretation is inherently difficult due to the need to detect motion into and out of the plane normal to observation. Imaging holding a piece of paper one meter in front of a physician's eyes and ask them to assess how far and in which direction it moves when the paper is moved 1-2 mm closer or further from their face. It is difficult and requires a trained eye. Algorithms can enable a nurse or minimally trained technician to interpret this exam with similar accuracy to that of an experienced physician.

The experimental cases detailed in FIG. 20 nicely tie all aspects of this project together. This data validates both the design of the Vortip specula, as well as the use of the automated pulse generator. The data in this figure provides a solid proof-of-concept on which to build. As hypothesized, the optimal configuration for deflection of a membrane in an unsealed condition is the Vortip speculum with automated pulse generation.

Safety: Since the products being developed in these efforts are medical devices, some discussion of safety is warranted. In short, short pulses of air with higher velocity is proposed than the slow squeeze currently used in pneumatic otoscopy that requires a canal seal. One of the first concerns is the question of safety. Two primary concerns arise: (1) will the force on the eardrum ever be large enough to cause damage or discomfort? and (2) what if the canal is sealed by accident?

When considering (1), the only time an unsafe force would be placed on the eardrum is in a failure case. The largest downside to the $CO_2$ cartridge automated stimulus design is that the worst fault case (regulator faulting to full-open) could result in damage to the patient's eardrum. This is an aspect that will be fully investigated in Phase II of this project. The actual risk involved is explored in such a design and its implications on product regulation from the FDA. The risk could be made sufficiently small such that this is not a significant concern. As a parallel effort, systems that can be "pumped up" by the user (similar to a blood pressure cuff) are investigated, and stored air can be delivered using the same regulator-style pulse delivery, without requiring a high pressure cartridge.

When considering (2), preliminary designs of specula with channels are tested that prevent the user from ever sealing the canal of the ear. A rendering of such a design can be seen in FIG. 7A-7B. Such a design ensures that any air delivered through the central bore of the tip will not be sent into a sealed canal. Although the air pulses used in these experiments were very low volume, if a fault case were to occur that caused a much larger volume of air to be ejected into the canal than expected, a sealed canal could potentially be dangerous to the patient due to rapid expansion of volume in the sealed canal. Preliminary tests of this anti-seal design show that no seal can be obtained in our canal models using these modified specula. This concept will be incorporated into the next iteration of Vortip designs.

FIG. 13. To increase patient safety during use of the Vortip and automated stimulus module, one way to prevent harm is to intelligently design the Vortip speculum to eliminate the risk of accidentally sealing the canal. An air escape channel like that depicted could be a good possible adaptation to our current designs.

CONCLUSION AND FUTURE WORK

This project investigated a potential solution to the problem that physicians currently have poor diagnostic accuracy when trying to assess fluid in the middle ear in cases of ear infections. Pneumatic otoscopy is the recommended method for detecting fluid in the ear, but few physicians perform it correctly due to the difficulty in obtaining a seal of the ear canal. A way to assess the mobility of the eardrum without requiring a seal of the canal was tested. By delivering a pulse of air that would move the eardrum upon contact, in contrast to the sealed-canal volume expansion method used in current pneumatic exams. A vortex ring delivered from a speculum tip would be a better method of delivering a pulse of air meant to move the eardrum than a simple jet. Both hypotheses were validated in the experiments detailed above.

In this project, novel Vortip specula were prototyped to validate vortex ring generation from an otoscope speculum form factor. Compared to current commercial tips, the Vortip was found to be superior at generating vortices, which led to increased membrane deflection when compared to standard commercial specula under identical stimulus conditions. A system for automated, controlled generation of air puffs was also built and validated as a method for accurate and precise stimuli, reducing user-variability. Finally, preliminary software algorithms were developed to automatically measure the deflection of eardrum phantoms during testing on current commercial video otoscopes using standard commercial specula and Vortips.

The promising results of this project are important to and align well with our company vision of enabling better ear disease diagnosis and management outcomes by developing superior tools for the medical professionals who manage these patients. This project proved the concept of simplified pneumatic otoscopy, resulting in multiple product opportunities. A suite of three products that could each stand alone, but when combined result in an optimized and superior solution. The first product is the Vortip specula, which enable the generation of vortex rings for pneumatic otoscopy without the requirement of a seal. This simplifies pneumatic otoscopy and can be used with any pneumatic otoscope. The challenge with this standalone product is subjectivity. While it simplifies the exam, it does not address the issues of user variability and interpretation of results that is highly expertise-dependent. The second product is a low-cost video pneumatic otoscope that enables automatic air pulse stimulus. As shown in this report, automated stimulus results in more efficient vortices and decreased user variability. The third product is a software package that analyzes the video feed from a video pneumatic otoscope and quantifies motion of the eardrum. A robust algorithmic approach will level the playing field and potentially enable a medical student trained in otoscopy to obtain results similar to that of an experienced physician. Each of these potential products has value to clinicians and patients. However, when combined, these three products will be an optimal solution for simple and accurate pneumatic otoscopy.

Further refinement of the automated stimulus module and the custom video analysis software is necessary. Future work on the automated stimulus module will include design reduction for a more compact form factor, possibly incorporating the module into a traditional or novel otoscope form factor. From our numerous customer discovery discussions with medical professionals who perform otoscopy, the major reasons why pneumatic otoscopy isn't performed, beyond difficulty with the ear canal seal, are difficulty locating where the pneumatic bulb attachment is in the office/clinic (i.e. don't have time to search) and issues pertaining to the pneumatic bulb attachment hanging off the otoscope (e.g. not easy to perform one-handed, children grabbing the bulb or attachment tube). Incorporating the pneumatic module inside the otoscope could directly remedy both of these issues. Future work on the custom video analysis software will include evaluation of more sophisticated techniques, such as developing an intensity based (e.g. cross-correlation) or feature-based (e.g. Scale-Invariant Feature Transform (SIFT) or Speeded Up Robust Features (SURF)) motion models. Considering that the rudimentary intensity-difference algorithm evaluated in this proposal gave a reasonable approximation of displacement, improvement in accuracy of displacement estimation in future work, enabled by these more robust algorithms.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

What is claimed is:

1. A speculum tip comprising:
    a cylindrical configuration including a narrow distal tip region longitudinally extending from a larger proximal region, wherein the distal tip region generates a toroidal vortex throughout a central shaft lumen coaxially disposed within the distal tip region; a distal end of the central shaft lumen includes a distal opening from which the toroidal vortex travels to displace a membrane; the proximal region includes a proximal opening operably coupled with a proximal lumen coaxially disposed within the proximal region as to receive a pulse of fluid; a proximal air escape outlet and a distal air escape inlet fluidly coupled with an air passageway therebetween as to prevent the speculum tip from sealing with the ear canal; the air passageway coaxially surrounds the central shaft lumen by a plurality of air passageways.

2. The speculum tip of claim 1, wherein the proximal lumen includes a cylindrical cross-section that narrows to a middle lumen, whereby the middle lumen transitions to the central shaft lumen.

3. The speculum tip of claim 2, wherein the central shaft lumen includes a diameter D1, and D1 is between about 0.1 to about 15 mm as to create the toroidal vortex exiting the distal opening.

4. The speculum tip of claim 3, wherein the diameter D1 produces a constant toroidal vortex with a diameter between about 0.1 to about 15 mm.

5. The speculum tip of claim 4, wherein the proximal lumen includes a proximal end with a diameter of D2 and the proximal lumen includes a distal end with a diameter of D3, wherein the diameter D2 is greater than the diameter D3, such that the proximal lumen includes a generally curved cross-section profile, and the diameter D2 is formatted as to fit a pneumatic otoscope and a pressure generator to generate the pulse of fluid.

6. The speculum tip of claim 1, wherein the distal end of the central shaft lumen is coupled to a proximal end of a distal lumen; the central shaft lumen includes a conical cross-section that narrows to the distal lumen; the distal lumen includes trapezoidal cross-section that includes a distal end larger than a proximal end; the distal end of the distal lumen includes the distal opening to generate an expanding toroidal vortex.

7. The speculum tip of claim 6, wherein the distal lumen includes an expanded tip cross-section, where the distal end of the distal lumen includes a diameter D4; the distal end of the central shaft lumen narrows to a diameter D5, wherein the distal end of the central shaft lumen coaxially aligns with the proximal end of the distal lumen; and the narrowing of the central shaft lumen to diameter D5 to generate the expanding toroidal vortex; and the diameter D4 is larger than the diameter D5.

8. The speculum tip of claim 7, wherein a proximal lumen includes a distal end with a diameter D6 that coaxially aligns with the proximal end of the central shaft lumen;
    the proximal lumen includes a proximal end with a diameter of D7; and the diameter D7 is larger or greater than the diameter D6 of the distal end of the proximal lumen, such that the proximal lumen includes a generally curved cross-section shape.

9. The speculum tip of claim 1, where the distal tip region includes a distal lumen lip coaxially disposed within the distal tip region; and the distal end of the central shaft lumen is coaxially coupled with the distal lip that surrounds the distal opening as to create a smaller distal opening than to the distal end of the central shaft lumen through which a focusing toroidal vortex displaces the eardrum without the requirement of a pressure seal of the ear canal.

10. The speculum tip of claim 9, wherein the central shaft lumen includes a diameter D8 that is narrowed by the distal end of the central shaft lumen; the distal lip includes a diameter D9 that creates a smaller distal opening than the diameter D8 of the distal end of the central shaft lumen, which produces a focusing diameter vortex ring.

11. The speculum tip of claim 10, wherein the diameter D9 is smaller than the diameter D8, and the ratio of D9:D8 is selected at ratio between about 1/4 and about 5/6.

12. A method of generating a toroidal vortex for a speculum tip, comprising the steps:
    generating a toroidal vortex through speculum tip comprising a cylindrical configuration with a narrow distal tip region longitudinally extending from a larger proximal region;
    passing a pulse of fluid through a generally central shaft lumen coaxially disposed within the distal tip region and a distal opening on a distal end of the central shaft lumen; preventing a seal of the speculum tip with the ear canal by coupling fluid to a proximal air escape outlet and a distal air escape inlet fluidly coupled with an air passageway therebetween; and
    displacing a membrane by the toroidal vortex exiting the distal opening without the requirement of a pressure seal of the ear canal; and
    measuring the displacement of the membrane.

13. The method of claim 12, further comprising:
    coupling the proximal region to an otoscope and a pressure generator.

14. The method of claim 13, further comprising selecting a diameter D1 of the central shaft lumen to produce a constant diameter toroidal vortex.

15. The method of claim 14, wherein the toroidal vortex includes a fluid burst of at least about 5 mmHg to about 100 mmHg to displace the tympanic membrane; and
diagnosing otitis media.

16. The method of claim 15, further comprising:
imaging the tympanic membrane with Optical Coherence Tomography.

17. The method of claim 16, wherein the toroidal vortex is selected from the group consisting of an expanding toroidal vortex, a focusing toroidal vortex, a constant diameter toroidal vortex, and a double concentric toroidal vortex.

* * * * *